(12) United States Patent
Hunt

(10) Patent No.: US 11,583,623 B2
(45) Date of Patent: Feb. 21, 2023

(54) COLLAPSIBLE STRUCTURE FOR WOUND CLOSURE AND METHOD OF USE

(71) Applicant: Smith & Nephew PLC, Watford (GB)

(72) Inventor: Allan Kenneth Frazer Grugeon Hunt, East Riding of Yorkshire (GB)

(73) Assignee: Smith & Nephew PLC, Watford (GB)

( * ) Notice: Subject to any disclaimer, the term of this patent is extended or adjusted under 35 U.S.C. 154(b) by 89 days.

(21) Appl. No.: 16/622,809

(22) PCT Filed: Jun. 11, 2018

(86) PCT No.: PCT/EP2018/065399
§ 371 (c)(1),
(2) Date: Dec. 13, 2019

(87) PCT Pub. No.: WO2018/229011
PCT Pub. Date: Dec. 20, 2018

(65) Prior Publication Data
US 2021/0146022 A1 May 20, 2021

Related U.S. Application Data

(60) Provisional application No. 62/519,768, filed on Jun. 14, 2017.

(51) Int. Cl.
*A61M 1/00* (2006.01)
*A61F 13/00* (2006.01)

(52) U.S. Cl.
CPC .......... *A61M 1/90* (2021.05); *A61F 13/00068* (2013.01)

(58) Field of Classification Search
CPC .......... A61F 13/00021; A61F 13/00029; A61F 13/00038; A61F 13/00051;
(Continued)

(56) References Cited

U.S. PATENT DOCUMENTS 2,245,909 A * 6/1941 Enfiajian ............ A61F 5/05816
128/DIG. 20
3,014,483 A 12/1961 Frank et al.
(Continued)

FOREIGN PATENT DOCUMENTS

AU 2012261793 A1 * 1/2013 .......... A61M 1/0088
AU 2012261793 B2 11/2014
(Continued)

OTHER PUBLICATIONS

International Search Report and Written Opinion for Application No. PCT/EP2018/065399, dated Jul. 27, 2018, 14 pages.
(Continued)

*Primary Examiner* — Nicholas J. Weiss
*Assistant Examiner* — Seth Han
(74) *Attorney, Agent, or Firm* — Knobbe, Martens, Olson & Bear, LLP

(57) ABSTRACT

In some embodiments, a negative pressure wound closure system and methods for using such a system are described. Certain disclosed embodiments facilitate closure of the wound by preferentially contracting to exert force on the tissue. Some embodiments may utilize a collapsible structure with a plurality of cells.

37 Claims, 22 Drawing Sheets

(58) Field of Classification Search
CPC .............. A61F 2013/0028; A61F 13/00; A61F 5/05808; A61F 5/05816; A61F 5/058; A61F 5/05825; A61F 5/05833; A61F 5/05841; A61F 5/0585; A61F 5/05858; A61F 5/05866; A61F 5/05875; A61F 5/05883; A61F 5/05891; A61F 5/34; A61F 5/32; A61F 5/30; A61F 5/012; A61F 5/0118; A61M 1/90; Y10S 128/20; A61B 17/1325; A61B 17/1322; A61B 17/1327; A61B 17/132; A61B 17/135

USPC ........................................................ 604/319

See application file for complete search history.

(56) References Cited

U.S. PATENT DOCUMENTS

| | | | |
|---|---|---|---|
| 3,164,152 A * | 1/1965 | Vere | A61F 5/05816 602/13 |
| 3,186,405 A * | 6/1965 | Bailey | A61F 5/05816 602/13 |
| 3,194,239 A | 7/1965 | Sullivan et al. | |
| 3,578,003 A | 5/1971 | Everett | |
| 3,789,851 A | 2/1974 | Leveen | |
| 3,812,616 A | 5/1974 | Koziol | |
| 4,467,805 A | 8/1984 | Fukuda | |
| 4,608,041 A | 8/1986 | Nielsen et al. | |
| 4,699,134 A | 10/1987 | Samuelsen | |
| 4,815,468 A | 3/1989 | Annand | |
| 5,176,663 A | 1/1993 | Svedman et al. | |
| 5,264,218 A | 11/1993 | Rogozinski | |
| 5,376,067 A * | 12/1994 | Daneshvar | A61B 17/1322 602/13 |
| 5,409,472 A | 4/1995 | Rawlings et al. | |
| 5,415,715 A | 5/1995 | Delage et al. | |
| 5,423,857 A | 6/1995 | Rosenman et al. | |
| 5,512,041 A | 4/1996 | Bogart | |
| 5,562,107 A | 10/1996 | Lavender et al. | |
| 5,584,859 A | 12/1996 | Brotz | |
| 5,636,643 A | 6/1997 | Argenta et al. | |
| 5,695,777 A | 12/1997 | Donovan et al. | |
| 5,810,750 A * | 9/1998 | Buser | A61F 5/05816 606/86 R |
| 6,176,868 B1 | 1/2001 | Detour | |
| 6,503,208 B1 | 1/2003 | Skovlund | |
| 6,548,727 B1 | 4/2003 | Swenson | |
| 6,566,575 B1 | 5/2003 | Stickels et al. | |
| 6,685,681 B2 | 2/2004 | Lockwood et al. | |
| 6,712,839 B1 | 3/2004 | Lonne | |
| 6,770,794 B2 | 8/2004 | Fleischmann | |
| 6,787,682 B2 | 9/2004 | Gilman et al. | |
| 6,883,531 B1 | 4/2005 | Perttu | |
| 6,977,323 B1 | 12/2005 | Swenson et al. | |
| 7,004,915 B2 | 2/2006 | Boynton et al. | |
| 7,144,390 B1 | 12/2006 | Hannigan et al. | |
| 7,315,183 B2 | 1/2008 | Hinterscher | |
| 7,351,250 B2 | 4/2008 | Zamierowski et al. | |
| 7,361,184 B2 | 4/2008 | Joshi et al. | |
| 7,438,705 B2 | 10/2008 | Karpowicz et al. | |
| 7,494,482 B2 | 2/2009 | Orgill et al. | |
| 7,615,036 B2 | 11/2009 | Joshi et al. | |
| 7,622,629 B2 | 11/2009 | Aali et al. | |
| 7,625,362 B2 | 12/2009 | Boehringer et al. | |
| 7,683,667 B2 | 3/2010 | Kim et al. | |
| 7,700,819 B2 | 4/2010 | Ambrosio et al. | |
| 7,754,937 B2 | 7/2010 | Boehringer et al. | |
| 7,779,625 B2 | 8/2010 | Joshi et al. | |
| 7,815,616 B2 | 10/2010 | Boehringer et al. | |
| 7,857,806 B2 | 12/2010 | Karpowicz et al. | |
| 7,863,495 B2 | 1/2011 | Aali | |
| 7,892,181 B2 | 2/2011 | Christensen et al. | |
| 7,896,856 B2 | 3/2011 | Petrosenko et al. | |
| 7,909,805 B2 | 3/2011 | Weston et al. | |
| 7,910,789 B2 | 3/2011 | Sinyagin | |
| 7,931,774 B2 | 4/2011 | Hall et al. | |
| 7,942,866 B2 | 5/2011 | Radl et al. | |
| 7,951,124 B2 | 5/2011 | Boehringer et al. | |
| 7,964,766 B2 | 6/2011 | Blott et al. | |
| 7,976,519 B2 | 7/2011 | Bubb et al. | |
| 7,976,524 B2 | 7/2011 | Kudo et al. | |
| 8,030,534 B2 | 10/2011 | Radl et al. | |
| 8,057,447 B2 | 11/2011 | Olson et al. | |
| 8,062,331 B2 | 11/2011 | Zamierowski et al. | |
| 8,067,662 B2 | 11/2011 | Aali et al. | |
| 8,070,773 B2 | 12/2011 | Zamierowski et al. | |
| 8,114,126 B2 | 2/2012 | Heaton et al. | |
| 8,123,781 B2 | 2/2012 | Zamierowski et al. | |
| 8,142,419 B2 | 3/2012 | Heaton et al. | |
| 8,172,816 B2 | 5/2012 | Kazala, Jr. et al. | |
| 8,187,237 B2 | 5/2012 | Seegert et al. | |
| 8,188,331 B2 | 5/2012 | Barta et al. | |
| 8,197,467 B2 | 6/2012 | Heaton et al. | |
| 8,207,392 B2 | 6/2012 | Haggstrom et al. | |
| 8,235,955 B2 | 8/2012 | Blott et al. | |
| 8,246,590 B2 | 8/2012 | Hu et al. | |
| 8,246,606 B2 | 8/2012 | Stevenson et al. | |
| 8,257,328 B2 | 9/2012 | Augustine et al. | |
| 8,273,105 B2 | 9/2012 | Cohen et al. | |
| 8,328,776 B2 | 12/2012 | Kelch et al. | |
| 8,337,411 B2 | 12/2012 | Nishtala et al. | |
| 8,353,931 B2 | 1/2013 | Stopek et al. | |
| 8,357,131 B2 | 1/2013 | Olson | |
| 8,376,972 B2 | 2/2013 | Fleischmann et al. | |
| 8,430,867 B2 | 4/2013 | Robinson et al. | |
| 8,447,375 B2 | 5/2013 | Shuler | |
| 8,454,990 B2 | 6/2013 | Canada et al. | |
| 8,460,257 B2 | 6/2013 | Locke et al. | |
| 8,481,804 B2 | 7/2013 | Timothy | |
| 8,486,032 B2 | 7/2013 | Seegert et al. | |
| 8,500,776 B2 | 8/2013 | Ebner | |
| 8,608,776 B2 | 12/2013 | Coward et al. | |
| 8,632,523 B2 | 1/2014 | Eriksson et al. | |
| 8,673,992 B2 | 3/2014 | Eckstein et al. | |
| 8,679,080 B2 | 3/2014 | Kazala, Jr. et al. | |
| 8,679,153 B2 | 3/2014 | Dennis | |
| 8,680,360 B2 | 3/2014 | Greener et al. | |
| 8,708,984 B2 | 4/2014 | Robinson et al. | |
| 8,721,629 B2 | 5/2014 | Hardman et al. | |
| 8,746,662 B2 | 6/2014 | Poppe | |
| 8,764,732 B2 | 7/2014 | Hartwell et al. | |
| 8,791,315 B2 | 7/2014 | Lattimore et al. | |
| 8,791,316 B2 | 7/2014 | Greener et al. | |
| 8,802,916 B2 | 8/2014 | Edward et al. | |
| 8,821,535 B2 | 9/2014 | Greener | |
| 8,945,030 B2 | 2/2015 | Weston et al. | |
| 9,039,783 B2 | 5/2015 | Petter-Puchner et al. | |
| 9,044,579 B2 | 6/2015 | Blott et al. | |
| 9,061,095 B2 | 6/2015 | Adie et al. | |
| 9,180,231 B2 | 11/2015 | Greener et al. | |
| 9,408,755 B2 | 8/2016 | Larsson et al. | |
| 9,421,132 B2 | 8/2016 | Dunn et al. | |
| 9,610,390 B2 | 4/2017 | Weston | |
| 9,655,807 B2 | 5/2017 | Locke et al. | |
| 9,801,986 B2 | 10/2017 | Greener | |
| 9,849,023 B2 | 12/2017 | Hall et al. | |
| 10,143,485 B2 | 12/2018 | Locke et al. | |
| 10,695,472 B2 | 6/2020 | Greener | |
| 11,058,807 B2 | 7/2021 | Weston | |
| 2001/0034499 A1 | 10/2001 | Sessions et al. | |
| 2002/0077661 A1 | 6/2002 | Saadat | |
| 2002/0161346 A1 | 10/2002 | Lockwood et al. | |
| 2004/0162512 A1 | 8/2004 | Liedtke et al. | |
| 2004/0267312 A1 | 12/2004 | Kanner et al. | |
| 2005/0142331 A1 | 6/2005 | Anderson et al. | |
| 2005/0267424 A1 | 12/2005 | Eriksson et al. | |
| 2006/0020269 A1 | 1/2006 | Cheng | |
| 2006/0058842 A1 | 3/2006 | Wilke et al. | |
| 2006/0069357 A1 | 3/2006 | Marasco | |
| 2006/0155260 A1 | 7/2006 | Blott et al. | |
| 2006/0217795 A1 | 9/2006 | Besselink et al. | |
| 2006/0271018 A1 | 11/2006 | Korf | |
| 2007/0052144 A1 | 3/2007 | Knirck et al. | |
| 2007/0104941 A1 | 5/2007 | Kameda et al. | |
| 2007/0118096 A1 | 5/2007 | Smith et al. | |

(56) References Cited

U.S. PATENT DOCUMENTS

| | | |
|---|---|---|
| 2007/0123973 A1 | 5/2007 | Roth et al. |
| 2007/0129660 A1 | 6/2007 | Mcleod et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0282309 A1 | 12/2007 | Bengtson et al. |
| 2008/0041401 A1 | 2/2008 | Casola et al. |
| 2008/0108977 A1 | 5/2008 | Heaton et al. |
| 2008/0243096 A1 | 10/2008 | Svedman |
| 2008/0275409 A1 | 11/2008 | Kane et al. |
| 2008/0306456 A1 | 12/2008 | Riesinger |
| 2009/0005716 A1 | 1/2009 | Abuzaina et al. |
| 2009/0099519 A1 | 4/2009 | Kaplan |
| 2009/0105670 A1 | 4/2009 | Bentley et al. |
| 2009/0204423 A1 | 8/2009 | Degheest et al. |
| 2009/0299308 A1* | 12/2009 | Kazala, Jr. .......... A61F 13/0289 604/319 |
| 2009/0312685 A1 | 12/2009 | Olsen et al. |
| 2010/0022990 A1 | 1/2010 | Karpowicz et al. |
| 2010/0047324 A1 | 2/2010 | Fritz et al. |
| 2010/0081983 A1 | 4/2010 | Zocher et al. |
| 2010/0137775 A1 | 6/2010 | Hu et al. |
| 2010/0150991 A1 | 6/2010 | Bernstein |
| 2010/0160874 A1 | 6/2010 | Robinson et al. |
| 2010/0179515 A1 | 7/2010 | Swain et al. |
| 2010/0198128 A1 | 8/2010 | Turnlund et al. |
| 2010/0262106 A1 | 10/2010 | Hartwell |
| 2010/0280468 A1 | 11/2010 | Haggstrom et al. |
| 2010/0312159 A1 | 12/2010 | Aali et al. |
| 2011/0021965 A1 | 1/2011 | Karp et al. |
| 2011/0022082 A1 | 1/2011 | Burke et al. |
| 2011/0059291 A1 | 3/2011 | Boyce et al. |
| 2011/0066096 A1 | 3/2011 | Svedman |
| 2011/0082480 A1 | 4/2011 | Viola |
| 2011/0110996 A1 | 5/2011 | Schoenberger et al. |
| 2011/0112458 A1 | 5/2011 | Holm et al. |
| 2011/0178451 A1 | 7/2011 | Robinson et al. |
| 2011/0213319 A1 | 9/2011 | Blott et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0264138 A1 | 10/2011 | Avelar et al. |
| 2011/0270301 A1 | 11/2011 | Cornet et al. |
| 2011/0305736 A1 | 12/2011 | Wieland et al. |
| 2012/0016321 A1 | 1/2012 | Wu et al. |
| 2012/0029455 A1 | 2/2012 | Perez-Foullerat et al. |
| 2012/0059412 A1 | 3/2012 | Fleischmann |
| 2012/0090699 A1* | 4/2012 | Lau ................ F16K 15/202 137/231 |
| 2012/0130327 A1 | 5/2012 | Marquez |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0172926 A1 | 7/2012 | Hotter |
| 2012/0191132 A1 | 7/2012 | Sargeant |
| 2012/0209226 A1 | 8/2012 | Simmons et al. |
| 2012/0209227 A1 | 8/2012 | Dunn et al. |
| 2012/0238931 A1 | 9/2012 | Rastegar et al. |
| 2012/0253302 A1 | 10/2012 | Corley |
| 2013/0012891 A1 | 1/2013 | Gross et al. |
| 2013/0023842 A1 | 1/2013 | Song |
| 2013/0066365 A1 | 3/2013 | Belson et al. |
| 2013/0150813 A1 | 6/2013 | Gordon et al. |
| 2013/0190705 A1 | 7/2013 | Vess et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0325142 A1 | 12/2013 | Hunter et al. |
| 2013/0331757 A1 | 12/2013 | Belson |
| 2014/0094730 A1 | 4/2014 | Greener et al. |
| 2014/0163415 A1 | 6/2014 | Zaiken et al. |
| 2014/0228732 A1* | 8/2014 | Steinbaugh ........ A61B 17/1322 602/53 |
| 2014/0228789 A1 | 8/2014 | Wilkes et al. |
| 2014/0249495 A1 | 9/2014 | Mumby et al. |
| 2015/0065968 A1 | 3/2015 | Sealy et al. |
| 2015/0119837 A1 | 4/2015 | Thompson, Jr. et al. |
| 2015/0157758 A1 | 6/2015 | Blücher et al. |
| 2015/0190288 A1 | 7/2015 | Dunn et al. |
| 2015/0196431 A1 | 7/2015 | Dunn et al. |
| 2015/0216732 A1 | 8/2015 | Hartwell et al. |
| 2015/0320602 A1 | 11/2015 | Locke et al. |
| 2015/0374561 A1 | 12/2015 | Hubbard, Jr. et al. |
| 2016/0144085 A1 | 5/2016 | Melin et al. |
| 2016/0184496 A1 | 6/2016 | Jaecklein et al. |
| 2017/0065751 A1 | 3/2017 | Toth et al. |
| 2017/0165116 A1* | 6/2017 | Dunn ................ A61F 13/00068 |
| 2017/0281838 A1 | 10/2017 | Dunn |
| 2020/0188564 A1 | 6/2020 | Dunn |
| 2020/0353136 A1 | 11/2020 | Greener |
| 2022/0001097 A1 | 1/2022 | Weston |

FOREIGN PATENT DOCUMENTS

| | | |
|---|---|---|
| AU | 2013206230 B2 | 5/2016 |
| CN | 101112326 A | 1/2008 |
| CN | 101744688 A | 6/2010 |
| CN | 201519362 U | 7/2010 |
| CN | 102038575 A | 5/2011 |
| CN | 202568632 U | 12/2012 |
| CN | 103071197 A | 5/2013 |
| CN | 203408163 U | 1/2014 |
| DE | 2949920 A1 | 3/1981 |
| EP | 1320342 A1 | 6/2003 |
| EP | 2185209 A2 | 5/2010 |
| EP | 2279016 A1 | 2/2011 |
| EP | 2567717 A1 | 3/2013 |
| EP | 2815731 A1 | 12/2014 |
| GB | 2389794 A | 12/2003 |
| GB | 2423019 A | 8/2006 |
| GB | 2489947 A | 10/2012 |
| GB | 2496310 A | 5/2013 |
| JP | S62-57560 A | 3/1987 |
| JP | 2006528038 A | 12/2006 |
| JP | 2009525087 A | 7/2009 |
| JP | 2012-105840 A | 6/2012 |
| RU | 1818103 A1 | 5/1993 |
| RU | 62504 U1 | 4/2007 |
| WO | WO 83/01388 A1 | 4/1983 |
| WO | WO 01/85248 A1 | 11/2001 |
| WO | WO 01/89392 A2 | 11/2001 |
| WO | WO 02/05737 A1 | 1/2002 |
| WO | WO 03/003948 A1 | 1/2003 |
| WO | WO 03/049598 A2 | 6/2003 |
| WO | WO 2005/046761 A1 | 5/2005 |
| WO | WO 2005/105174 A1 | 11/2005 |
| WO | WO 2006/046060 A2 | 5/2006 |
| WO | WO 2008/027449 A2 | 3/2008 |
| WO | WO 2008/064502 A1 | 6/2008 |
| WO | WO 2008/104609 A1 | 9/2008 |
| WO | WO 2009/112062 A1 | 9/2009 |
| WO | WO 2010/033725 A2 | 3/2010 |
| WO | WO 2010/097570 A1 | 9/2010 |
| WO | WO 2011/023384 A1 | 3/2011 |
| WO | WO 2012/082716 A2 | 6/2012 |
| WO | WO 2012/082876 A1 | 6/2012 |
| WO | WO 2012/136707 A1 | 10/2012 |
| WO | WO 2012/142473 A1 | 10/2012 |
| WO | WO 2013/012381 A1 | 1/2013 |
| WO | WO 2013/043258 A1 | 3/2013 |
| WO | WO 2013/071243 A2 | 5/2013 |
| WO | WO 2013/076450 A1 | 5/2013 |
| WO | WO 2013/079947 A1 | 6/2013 |
| WO | WO 2013/175309 A1 | 11/2013 |
| WO | WO 2013/175310 A2 | 11/2013 |
| WO | WO 2014/013348 A2 | 1/2014 |
| WO | WO 2014/140578 A1 | 9/2014 |
| WO | WO 2014/158526 A1 | 10/2014 |
| WO | WO 2014/165275 A1 | 10/2014 |
| WO | WO 2014/178945 A1 | 11/2014 |
| WO | WO 2014/194786 A1 | 12/2014 |
| WO | WO 2015/008054 A1 | 1/2015 |
| WO | WO 2015/061352 A2 | 4/2015 |
| WO | WO 2015/109359 A1 | 7/2015 |

(56) References Cited

FOREIGN PATENT DOCUMENTS

| WO | WO 2015/110409 A1 | 7/2015 |
| --- | --- | --- |
| WO | WO 2015/110410 A1 | 7/2015 |
| WO | WO 2015/169637 A1 | 11/2015 |
| WO | WO 2015/193257 A1 | 12/2015 |
| WO | WO 2016/018448 A1 | 2/2016 |
| WO | WO 2016/176513 A1 | 11/2016 |
| WO | WO 2016/179245 A1 | 11/2016 |
| WO | WO 2017/106576 A1 | 6/2017 |
| WO | WO 2018/038665 A1 | 3/2018 |
| WO | WO 2018/041805 A1 | 3/2018 |
| WO | WO 2018/044944 A1 | 3/2018 |
| WO | WO 2018/044949 A1 | 3/2018 |
| WO | WO 2018/085457 A1 | 5/2018 |
| WO | WO 2018/140386 A2 | 8/2018 |
| WO | WO 2018/237206 A2 | 12/2018 |

OTHER PUBLICATIONS

"Definition of 3D Printer," American Heritage Dictionary of the English Language, Fifth Edition, accessed on Feb. 22, 2018 from URL: https://www.thefreedictionary.co, 2016, 1 page.

"Definition of Adhere," The Free Dictionary, accessed on Mar. 23, 2017 from http://www.thefreedictionary.com/adhere, 6 pages.

"Definition of Oculiform," Webster's Revised Unabridged Dictionary, accessed from The Free Dictionary on May 30, 2018 from URL: https://www.thefreedictionary.com/Oculiform, 1913, 1 page.

"Definition of Throughout," Merriam-Webster Dictionary, accessed on Aug. 29, 2017 from https://www.merriam-webster.com/dictionary/throughout, 11 pages.

Hougaard, et al., "The Open Abdomen: Temporary Closure with a Modified Negative Pressure Therapy Technique," International Wound Journal, ISSN 1742-4801, 2014, pp. 13-16.

Kapischke M., et al., "Self-Fixating Mesh for the Lichtenstein Procedure—a Prestudy," Langenbecks Arch Surg, 2010, vol. 395, pp. 317-322.

International Preliminary Reporton Patentability for Application No. PCT/EP2018/065399, dated Dec. 26, 2019, 10 pages.

U.S. Appl. No. 12/922,118, Vacuum Closure Device, filed Nov. 17, 2010.

U.S. Appl. No. 14/466,892, Vacuum Closure Device, filed Aug. 22, 2014.

U.S. Appl. No. 15/796,441, Vacuum Closure Device, filed Oct. 27, 2017.

U.S. Appl. No. 16/879,466, Vacuum Closure Device, filed May 20, 2020.

U.S. Appl. No. 16/637,258, Wound Closure Device With Protective Layer and Method of Use, filed Feb. 6, 2020.

U.S. Appl. No. 14/610,806, Negative Pressure Dressing and Method of Using Same, filed Jan. 30, 2015.

U.S. Appl. No. 15/441,899, Negative Pressure Dressing and Method of Using Same, filed Feb. 24, 2017.

U.S. Appl. No. 17/372,191, Negative Pressure Dressing and Method of Using Same, filed Jul. 9, 2021.

U.S. Appl. No. 12/922,130, Negative Pressure Dressing and Method of Using Same, filed Nov. 16, 2010.

* cited by examiner

COLLAPSIBLE STRUCTURE FOR WOUND CLOSURE AND METHOD OF USE

CROSS-REFERENCE TO RELATED APPLICATIONS

This application is a U.S. national stage application of International Patent Application No. PCT/EP2018/065399, filed Jun. 11, 2018, which claims priority to U.S. Provisional Application No. 62/519,768 filed on Jun. 14, 2017, which is incorporated by reference in its entirety.

BACKGROUND

Field of Use

This application describes embodiments of apparatuses, methods, and systems for the treatment of wounds, specifically to aid in the closure of large wounds.

Description of the Related Art

Amputation of lower and upper extremities is one of the oldest known surgically performed procedures. The vast majority of amputations are performed because of atherosclerosis, which is a symptom of diabetes. Less commonly, serious accidents, cardiovascular disease, or the development of a tumor in a limb can lead to the loss of a limb. Amputation procedures require the removal of the diseased tissue in addition to the cutting and shaping of muscle, therefore a large wound is necessarily created on the patient. Closure of such a wound after the underlying edema has subsided, while minimizing the risk of secondary infections and other complications, then becomes a priority.

Other large or incisional wounds at extremities, either as a result of surgery, trauma, or other conditions, may also require closure. Wound dehiscence of existing wounds is another complication that may arise, possibly due to incomplete underlying fascial closure, or secondary factors such as infection.

The treatment of open or chronic wounds by means of applying negative pressure to the site of the wound, where the wounds are too large to spontaneously close or otherwise fail to heal is well known in the art. Negative pressure, in many cases, can improve the rate of healing while also removing exudates and other deleterious substances from the wound. Negative pressure wound treatment systems currently known in the art commonly involve placing a cover that is impermeable to liquids over the wound, using various mechanisms to seal the cover to the tissue of the patient surrounding the wound, and connecting a source of negative pressure (such as a vacuum pump) to the cover whereby an area of negative pressure is created under the cover in the area of the wound.

However, existing negative pressure treatment systems, while permitting eventual wound closure, still require lengthy closure times. Although these may be combined with other tissue securement means, such as sutures, there is also a risk that underlying muscular and fascial tissue is not appropriately reapproximated so as to permit complete wound closure. Further, when foam or other wound fillers are inserted into the wound, the application of negative pressure to the wound and the foam may cause atmospheric pressure to bear down onto the wound, compressing the foam downward and outward against the margins of the wound. This downward compression of the wound filler slows the healing process and slows or prevents the joining of wound margins. Additionally, inflammation of the fascia in the form of certain types of fasciitis can lead to rapid and excessive tissue loss, potentially meriting the need for more advanced negative pressure treatment systems. Accordingly, there is a need to provide for an improved apparatus, method, and system for the treatment and closure of wounds.

SUMMARY

Certain disclosed embodiments relate to negative pressure wound closure devices, methods, and systems that facilitate closure of a wound. It will be understood by one of skill in the art that the wounds described herein this specification may encompass any wound, and are not limited to a particular location or type of wound. Further, it will be understood by one of skill of art that application of the devices, methods, and systems described herein are not limited to the closure of wound or any other particular use. The devices, methods, and systems may operate to reduce the need for repetitive replacement of wound filler material currently employed and can advance the rate of healing. The devices, methods, and systems may be simultaneously used with negative pressure to remove wound fluids.

In some embodiments, a wound closure device may comprise a collapsible structure, the collapsible structure comprising:
  a top layer and a bottom layer, wherein the top layer and the bottom layer are partially adhered to each other;
  a volume between the top layer and the bottom layer;
  a plurality of elongate cells each having a length and a width, the plurality of elongate cells arranged side-by-side in at least a portion of the volume, the cells in the plurality of elongate cells arranged parallel to one another,
  wherein said plurality of elongate cells are defined by at least one of the top layer or the bottom layer, and
  wherein at least one of the cells is inflatable.

The collapsible structure may be configured to collapse under negative pressure when at least one of the cells is deflated. The collapsible structure may be configured to collapse along its length. The top layer and the bottom layer may comprise flexible film material. The length of each cell may be greater than its width.

In some embodiments, the collapsible structure may have at least partially a cylindrical shape, and wherein the cells are arranged with their widths positioned substantially annularly around a circular side of the cylindrical shape. The collapsible structure may be closed at one end of the cylindrical shape.

The collapsible structure may further comprise an intermediate layer, wherein each cell is defined by the intermediate layer and either one of the top layer or the bottom layer, and wherein the intermediate layer is at least partially adhered to each of the top layer and the bottom layer. The top layer, the bottom layer and an intermediate layer may be at least partially adhered to each other by welding. The welding may be selected from the group consisting of heat welding, radio frequency welding, laser welding, and ultrasonic welding.

In some embodiments, the collapsible structure may further comprise a fluid channel configured to fluidically connect said plurality of cells with an environment exterior to the collapsible structure. At least one of the cells may comprise a seal and/or a valve between the fluid channel and the cell, wherein the valve is configured to permit fluid flow only from the fluid channel to the cell but not in the other direction.

In some embodiments, at least one of the cells may comprise a pull-off tab configured to provide a fluidic connection between the cell and environment exterior to the collapsible structure. The pull-off tab may be configured to be reversible.

In some embodiments, the wound closure device may further comprise a tissue protection layer, one or more drapes configured to cover the collapsible structure and form a seal around a wound, and/or a suction port configured to supply negative pressure to the wound. The device may further comprise a negative pressure source configured to supply negative pressure to the collapsible structure to cause collapse of the collapsible structure and cause the collapsible structure to apply a force to the wound.

In some embodiments, a method of treating a wound may comprise providing a collapsible structure of any one of the preceding claims; and placing the collapsible structure in or over the wound so that the collapsible structure is aligned along its length with a length of the wound. The method may further comprise applying negative pressure through the collapsible structure to the wound via a source of negative pressure, wherein the application of negative pressure causes the collapsible structure to collapse and/or inserting a tissue protection layer over the wound before placing the collapsible structure.

Other embodiments of an apparatus for use with negative pressure, devices, kits and associated methods are described below.

DETAILED DESCRIPTION

Figure 1:
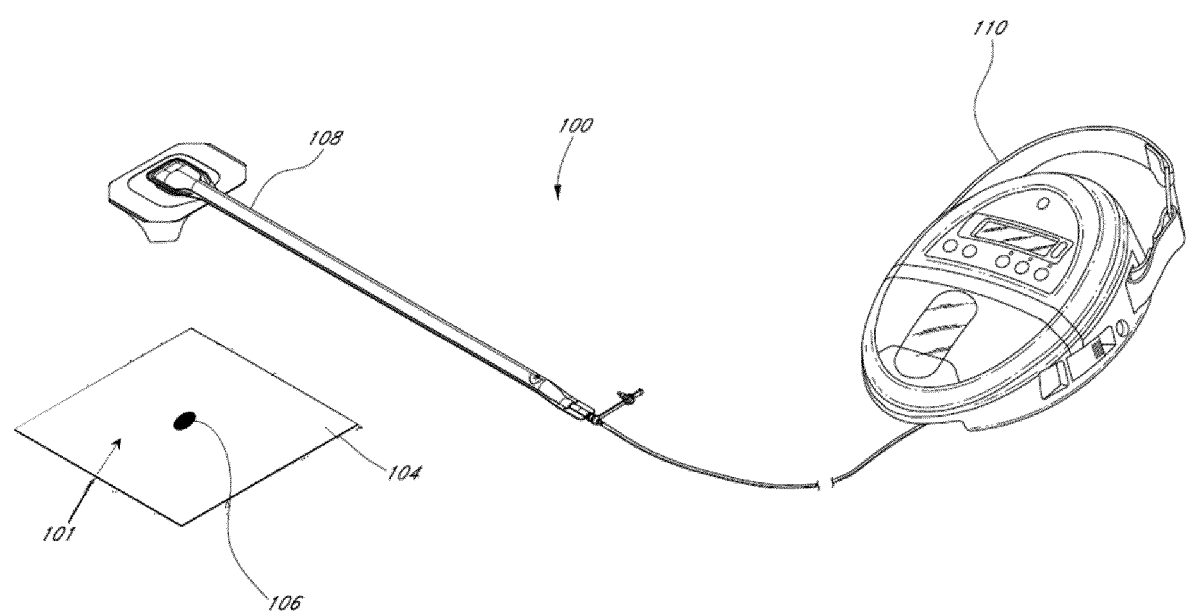
FIG. 1 illustrates an embodiment of a negative pressure treatment system.

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that, in some cases, benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, amputation wounds, flaps and skin grafts, lacerations, abrasions, contusions, burns, electrical burns, diabetic ulcers, pressure ulcers, stoma, surgical wounds, trauma and venous ulcers or the like.

As is used in this section or elsewhere in this specification, reduced or negative pressure levels, such as −X mmHg, represent pressure levels that are below standard atmospheric pressure, which typically corresponds to 760 mmHg (or 1 atm, 29.93 inHg, 101.325 kPa, 14.696 psi, etc.). Accordingly, a negative pressure value of −X mmHg reflects absolute pressure that is X mmHg below, for example, 760 mmHg or, in other words, an absolute pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −10 mmHg and −200 mmHg Note that these pressures are relative to normal ambient atmospheric pressure. Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus. In some embodiments, the negative pressure range can be as small as about −20 mmHg or about −25 mmHg, which may be useful to reduce fistulas. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat).

Examples of such applications where additional disclosure relating to the preceding descriptions may be found include U.S. Pat. No. 8,235,955, titled "Wound treatment apparatus and method," issued Aug. 7, 2012 and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described in this section or elsewhere in this specification may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227, the entireties of each of which are hereby incorporated by reference. Still more applications that may contain teachings relevant for use with the embodiments described in this specification are application Ser. No. 13/942,493, titled "Negative Pressure Wound Closure Device," filed Jul. 15, 2013, published as US 2014/0180225; PCT App. No. PCT/US2013/050619, filed Jul. 16, 2013 titled "Negative Pressure Wound Closure Device," published as WO 2014/014871 A1; PCT App. No. PCT/US2013/050698, filed Jul. 16, 2013 titled "Negative Pressure Wound Closure Device," published as WO 2014/014922 A1; PCT App. No. PCT/IB2013/01555, titled "Devices and Methods for Treating and Closing Wounds with Negative Pressure," filed May 5, 2013, published as WO 2013/175309 A1; PCT App. No. PCT/US2014/025059, titled "Negative Pressure Wound Closure Device and Systems and Methods of Use in Treating Wounds with Negative Pressure," filed Mar. 12, 2014, published as WO 2014/165275 A1; PCT App. No. PCT/GB2014/050746, "Compressible Wound Fillers and Systems and Methods of Use In Treating Wounds With Negative Pressure," filed Mar. 13, 2014, published as WO 2014/140578 A1; PCT App. No. PCT/US2014/061627, titled "Negative Pressure Wound Closure Device," filed Oct. 21, 2014, and published as 2016/0287765 A1; and PCT App. No. PCT/US2016/029888, titled "Negative Pressure Wound Closure Device," filed Apr. 28, 2016, published as WO 2016/176513. Each of the aforementioned applications is hereby incorporated by reference in it entirety and should be considered part of the present specification.

As used in this section or elsewhere in this specification, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal," and "lateral" may also be used to describe the collapsible structures and wound closure devices described throughout this specification. When describing these structures or devices, these terms should not be construed to require that the structures or devices necessarily be placed into a wound in a certain orientation, though in certain embodiments, it may be preferable to do so.

FIG. 1 illustrates an embodiment of a negative pressure treatment system 100 that comprises a wound closure device 104 in and/or over a wound 101. The wound closure device 104 may comprise one or more embodiments of collapsible structures described in further detail in this section or elsewhere in this specification. In some embodiments, a single drape or multiple drapes (not shown here) may be placed over the wound closure device 104, and is preferably adhered or sealed to the skin on the periphery of the wound 101 so as to create a fluid-tight seal. An aperture 106 may be made through the wound closure device 104 or the drape, which can be manually made or preformed into the wound closure device 104 or drape so as to provide a fluidic connection from the wound 101 to a source of negative pressure such as a pump 110. Preferably, the fluidic connection between the aperture 106 and the pump 110 is made via a conduit 108. In some embodiments, the conduit 108 may comprise a RENASYS® Soft Port™, manufactured by Smith & Nephew. Of course, in some embodiments, the wound closure device 104 or the drape may not necessarily comprise an aperture 106, and the fluidic connection to the pump 110 may be made by placing the conduit 108 below the wound closure device 104 or the drape. In some wounds, particularly larger wounds, multiple conduits 108 may be used, fluidically connected via one or more apertures 106.

In use, the wound 101 may be prepared and cleaned. In some cases, a non- or minimally-adherent tissue protection layer (not illustrated) may be applied over any exposed internal tissue. The wound 101 is then covered with wound closure device 104, optionally so as to form a fluid-tight seal. In some embodiments, the wound 101 and the wound closure device 104 further covered with the drape so as to form a fluid-tight seal. A first end of the conduit 108 is then placed in fluidic communication with the wound, for example via the aperture 106. The second end of the conduit 108 is connected to the pump 110. The pump 110 may then be activated so as to supply negative pressure to the wound 101 and evacuate wound exudate from the wound 101. As will be described in additional detail herein and in relation to the embodiments of the foregoing wound closure devices, negative pressure may also aid in promoting closure of the wound 101, for example by approximating opposing wound margins.

Any structure or component disclosed in this section or elsewhere in the specification may comprise a radiopaque material. A radiopaque material advantageously allows a clinician to more easily find pieces of the wound closure device that may have come loose from the structure and become lost in the wound. Some examples of radiopaque materials include barium sulfate, bismuth trioxide, bismuth subcarbonate, bismuth oxychloride, and tungsten.

Collapsible Structures

Figure 2A:
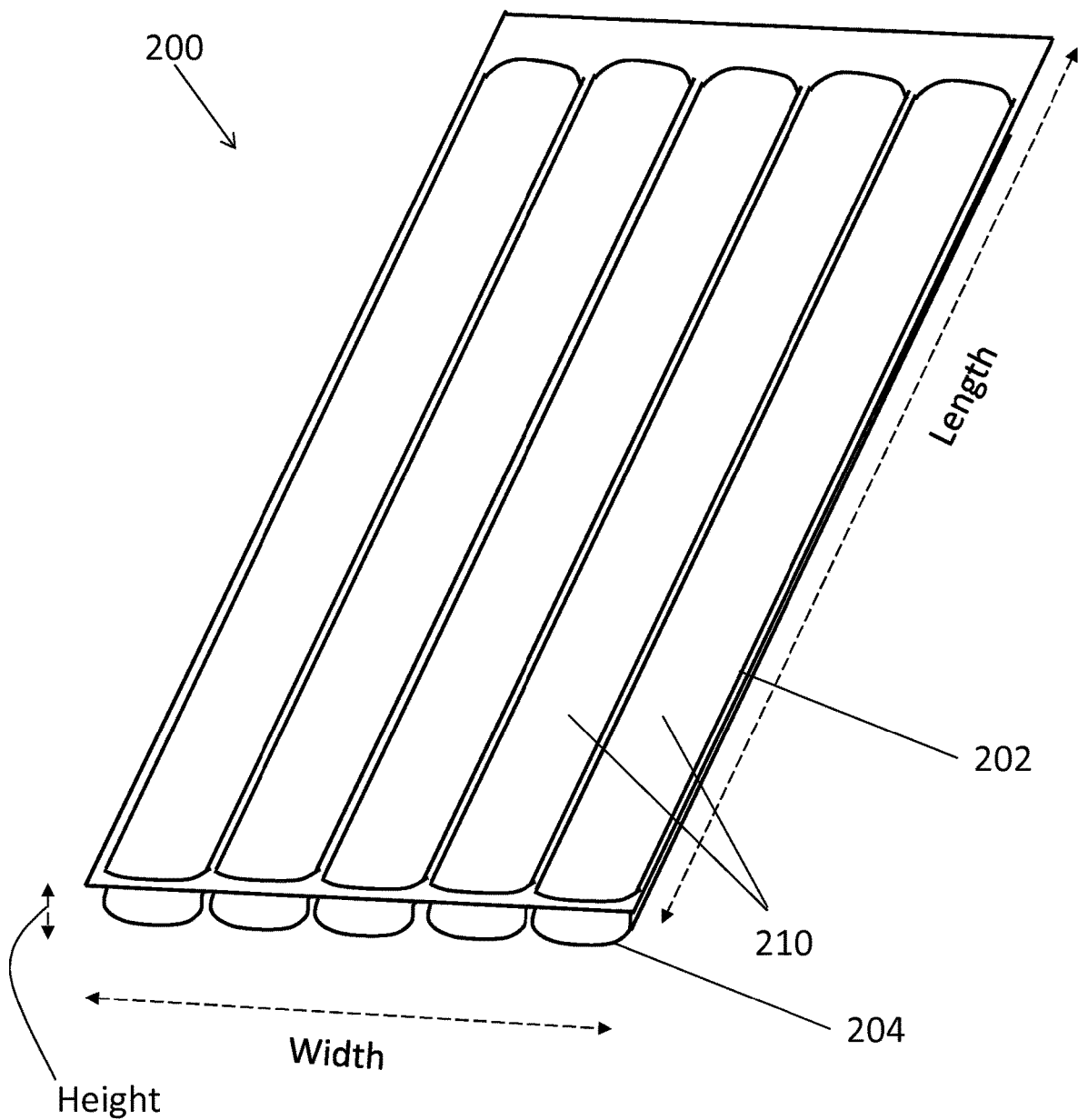
FIG. 2A illustrates a perspective view of an embodiment of a collapsible structure.
Figure 2B:
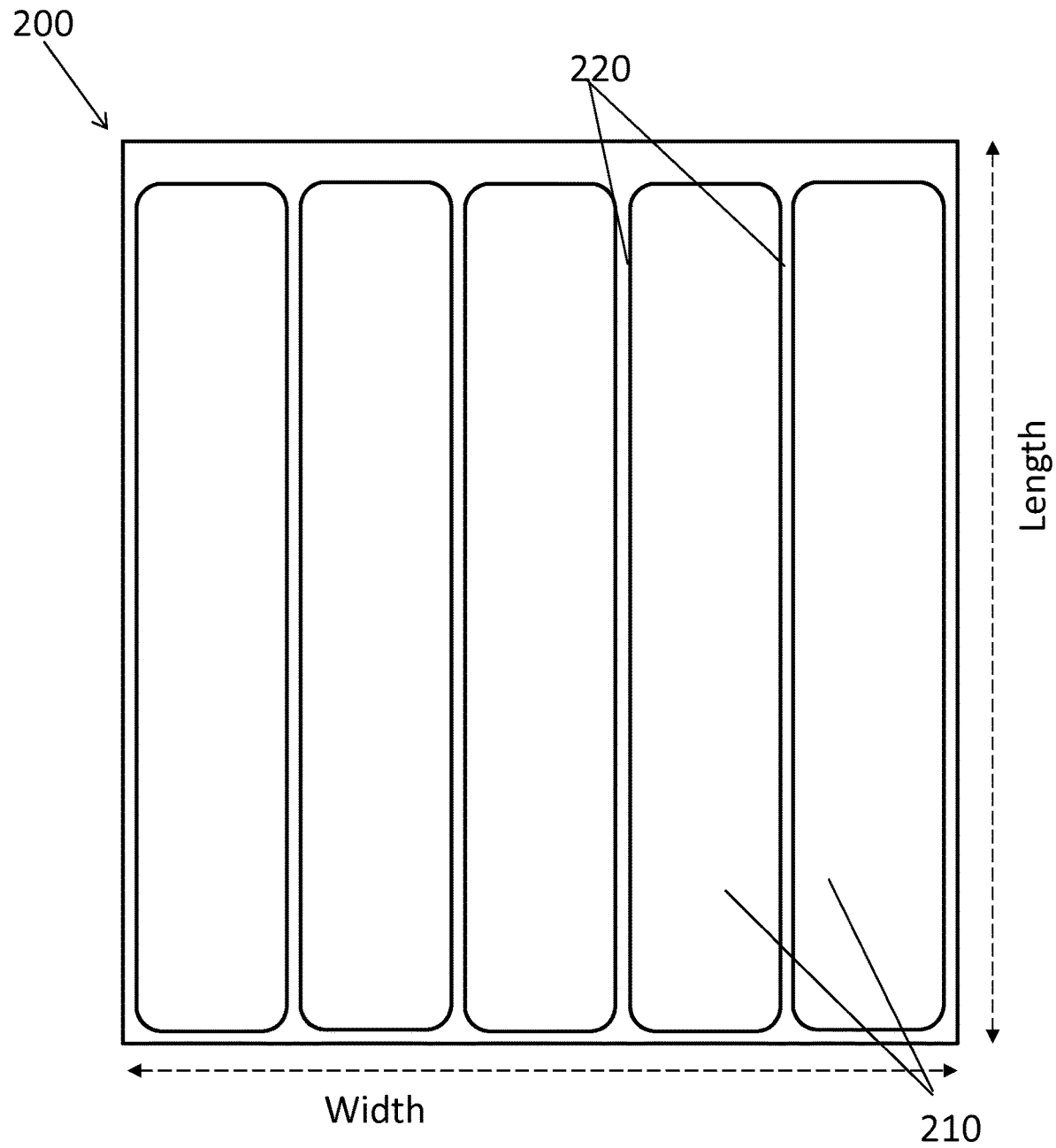
FIG. 2B illustrates a top view of the collapsible structure of FIG. 2A.
Figure 2C:
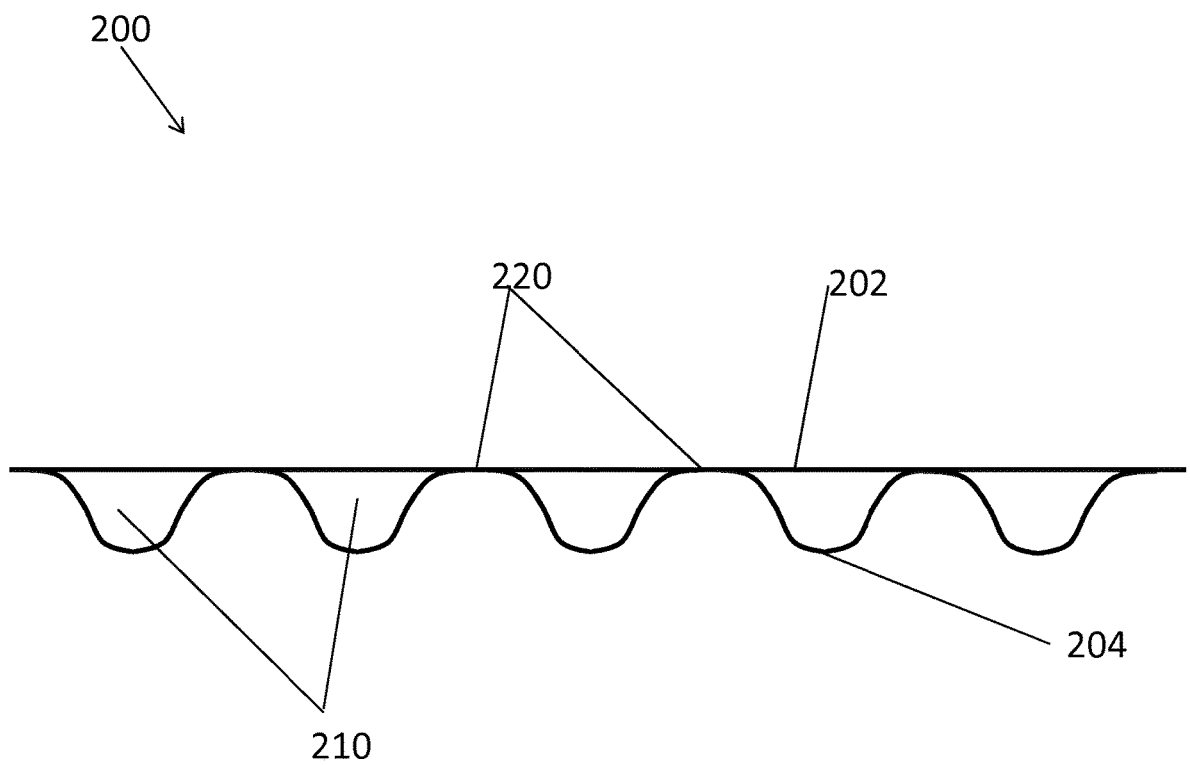
FIG. 2C illustrates a cross-sectional view of the collapsible structure of FIG. 2A.
Figure 3:
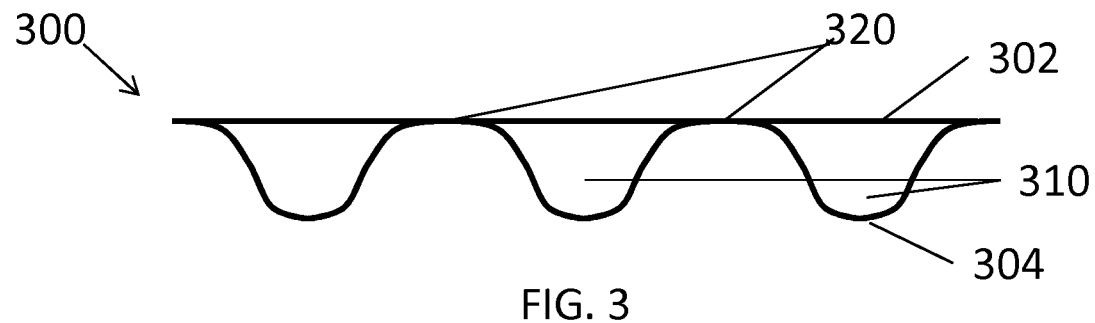
FIGS. 3-7 illustrate cross sectional view of embodiments of a collapsible structure.

A wound closure device as described in this section or elsewhere in the specification may include a collapsible sheet or structure, which may be an enclosure for a wound. FIGS. 2A-C illustrate an embodiment of a collapsible structure 200. FIG. 2A-C illustrate a perspective view, a top view, and a cross sectional view along the width of the collapsible structure 200. The collapsible structure 200 may include a top layer 202, a bottom layer 204, and a plurality of elongate cells 210 provided side-by-side. The plurality of elongate cells 210 may be defined by the top layer 202, the bottom layer 204, and a plurality of valleys 220 where the top layer 202 and the bottom layer 204 meets. The elongate cells 210 may be longer in their lengths than widths, and arranged side-by-side lengthwise.

All collapsible structures described herein this section or elsewhere in the specification may be fashioned to accommodate any size of wound. However, to better accommodate the needs of the clinical environment, in certain embodiments, collapsible structuress described herein may be provided in a pack of two sizes, one smaller collapsible structure and one larger collapsible structure about 1.25 times as larger, about 1.5 times as large, about 1.75 times as large, about 2 times as larger, about 2.5 times as larger, about 3 times as large, about 4 times as large, about 5 times as large, or more than about 5 times as large. In some embodiments, the pack may comprise more than two sizes, such as three sizes, four sizes, five sizes, or more than five sizes. The collapsible structure within the pack may be of a variety of sizes in relation to one another such as the ratios described herein. In some embodiments, a large collapsible structure may be provided, such that it can be cut into a desirable size, or torn along an optional pre-cut.

Collapsible structures described in this section or elsewhere in the specification, may be applied on the wound. In some embodiments, a tissue protection layer may be placed or positioned in and/or on the wound, before placement of the collapsible structure. In some embodiments, the collapsible structure may be adhered or sealed to the skin on the periphery of the wound so as to create a fluid-tight seal, and the negative pressure may be provided beneath the collapsible structure. In some embodiments, the drape may be provided above the collapsible structure and may be adhered or sealed to the skin on the periphery of the wound so as to create a fluid-tight seal, and the negative pressure may be provided beneath the drape and/or the collapsible structure.

In certain embodiments, the collapsible structure 200 can collapse in any manner described in this section or elsewhere in this specification with or without the application of negative pressure. For example, the collapsible structure may collapse significantly more in one direction than in another direction, upon application of negative pressure. In some embodiments, the collapsible structure may collapse more in the width than in length. In embodiments, particular cells may collapse in a first direction, while other cells may collapse in the same or other direction. The collapsible structure may be constructed from any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam. In certain embodiments, the collapsible structure may comprise a radio opaque material, to more readily allow a clinician to find pieces of the collapsible structure within the wound.

Returning to FIGS. 2A-C, the collapsible structure 200 may have an outer perimeter that defines a rectangular shape such as shown in FIGS. 2A-B. However, the collapsible structure 200 may have various shapes to better accommodate various shapes of wounds. For example, the collapsible structure 200 may be at least partially circular, hexagonal, elliptical, diamond-shaped, or the like. In some embodiments, the collapsible structure 200 may be shaped as an enclosure having a three-dimensional shape. For example, the collapsible structure 200 may have at least partially annular shaped, such that it can be applied around cylindrical body parts (e.g., limbs) as described elsewhere in the specification in greater detail.

As described herein, the collapsible structure 200 may comprise a plurality of elongate cells 210 provided side-by-side. As with the other collapsible structures described herein this section and elsewhere in the specification, the collapsible structure 200 may collapse by collapsing one or more cells 210. In some embodiments, the cells 210 are all of the same approximate shape and/or size; however, in other embodiments, at least some of the cells are of different shapes and/or sizes. In some embodiments, the collapsible structures as described herein this section or elsewhere in the specification may have rectangular shape, in which the cells are arranged parallel to one another along their length, such as shown in FIGS. 2A-B. However, the cells may have other shapes, such as elliptical, diamond, or another suitable shape. In some embodiments, the collapsible structure may have cells with two or more different types of shapes provided side-by side.

In some embodiments, the cells 210 are inflatable. The collapsible structure 200 may be at least partially constructed from flexible film material, for example polyurethane, such that cells 210 may be filled with fluid, such as air, and inflated. In some embodiments, the collapsible structure 200 is constructed from one or more fluid-tight materials, such that cells 210 are fludically isolated and remain inflated for prolonged period. In some embodiments, the top layer 202 and the bottom layer 204 are each constructed from flexible film material, for example polyurethane, and adhered to one another for example by adhesive, heat welding, radio frequency welding, laser welding, or ultrasonic welding at valley 220. The top layer 202, the bottom layer 204, or any other part of the collapsible structure may be configured to withstand the fluid pressure within inflated cells, such that cells do not burst without puncturing or cutting. In some embodiments, the collapsible structure 200 may include a valve, a port, or any other suitable mechanism, such that cells can be reversibly and/or selectively inflated, as described elsewhere in the specification in greater detail.

The collapsible structure 200 may be made from one single material, such as those described elsewhere in the specification, or the collapsible structure 200 may be made from multiple materials. For example, the top layer 202 may be constructed from more rigid material while the bottom layer 204 may be constructed from more flexible material. In some embodiments, the top layer 202 and/or the bottom layer 204 may have embossed surface as cells 210 are inflated and bulged out. In some embodiments, the top layer 202 and/or the bottom layer 204 may be flat in their natural state, but constructed from flexible material such that cells 210 can be bulged out on their top and/or bottom end when cells are inflated.

In some embodiments, the collapsible structure 200 of FIG. 2A-2C includes perforations or detachable sections that allow portions of the structure to separate from the remainder of the device. For example, perforations may be incorporated into valleys 220 between cells 210 contained within the collapsible structure 200, allowing for the removal of individual cells to alter the shape or size of the collapsible structure 200. Applicable to all collapsible structure or wound closure devices described in this section or elsewhere in the specification, the collapsible structure or wound closure device may be tearable such that the collapsible structure may be shaped into the shape of a wound. In some embodiments, the collapsible structure may be torn along the cell wall, while in further embodiments, the elongate strips or intervening members may be torn at any suitable position.

FIGS. 3-7 illustrate collapsible structures similar to the collapsible structure described in relation with FIGS. 2A-2C or elsewhere in the specification, but having different configurations. In the embodiment illustrated in FIG. 3, a collapsible structure 300 is constructed from a top layer 302 and a bottom layer 304 adhered to each other at valleys 320.

Figure 4:
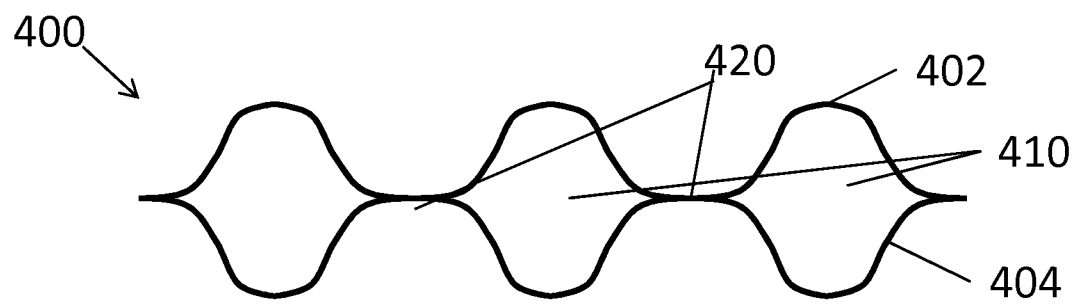

The top layer 302 is relatively flat while the bottom layer 304 is relatively bulged from inflated cells 320. The top layer 302 may be constructed from a more rigid material than then bottom layer 304, such that it can stay relatively flat when cells 320 inflate. Such configuration may help the collapsible structure having more protection from the outside environment, when the collapsible structure is applied on the wound, the bottom layer facing the wound. In some embodiments, the top layer 302 may be relatively bulged, which the bottom layer 304 is relatively flat. FIG. 4 illustrates a collapsible structure 400 similar to the collapsible structure 300 of FIG. 3 according to one embodiment. Here, both the top layer 402 and the bottom layer 404 are bulged. In some embodiments, the top layer 402 and the bottom layer 404 are identical, such that the collapsible structure 400 is reversible.

Figure 5:
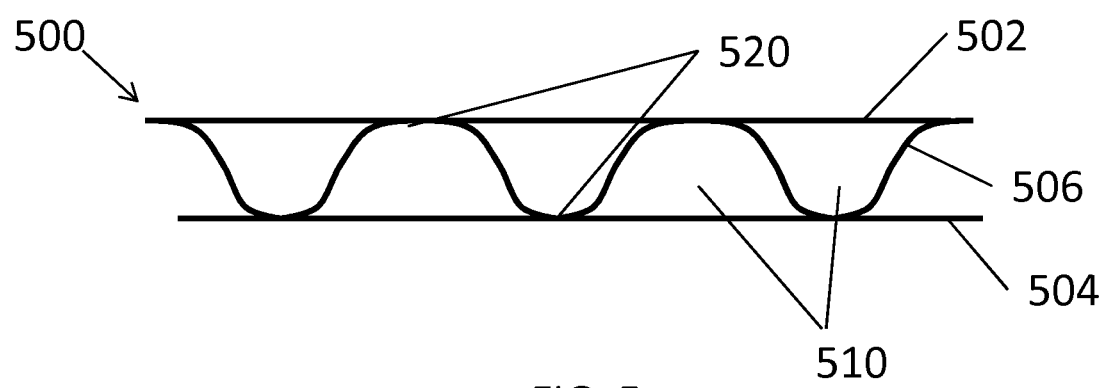
Figure 6:
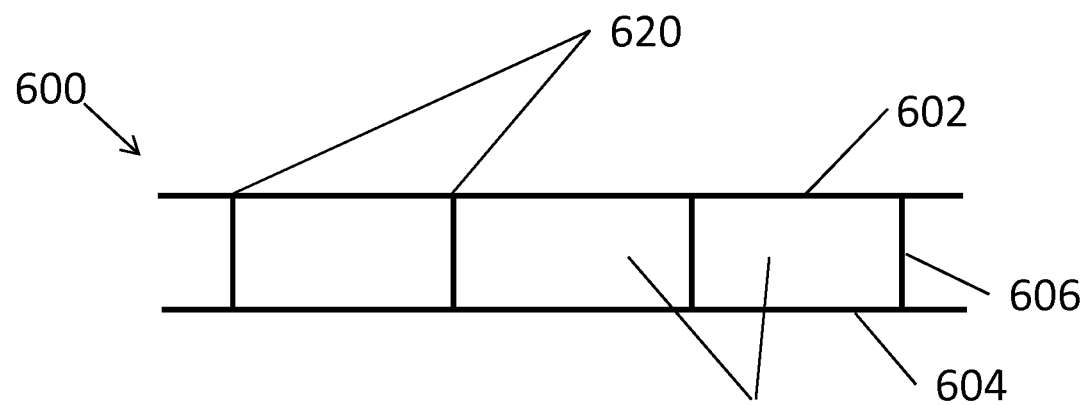
Figure 7:
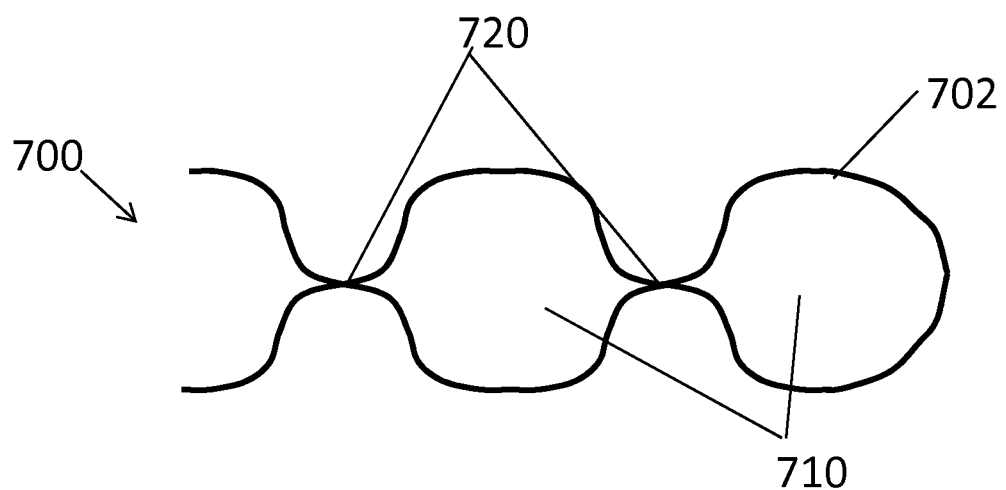

Collapsible structures may have more than two layers (i.e. the top layer and the bottom layer). For example, a collapsible structure may be constructed from three, four, five or more layers. FIG. 5 illustrates an embodiment of a collapsible structure 500 having a top layer 502, a bottom layer 504 and an intermediate layer 506. The intermediate layer 506 is adhered to the top layer 502 or the bottom layer 504 at valleys 520, and cells 510 are defined by the intermediate layer 506 and the top layer 502 or the bottom layer 504. Instead of having a continuous intermediate layer such as shown in FIG. 5, a collapsible structure may have discontinuing cell walls. FIG. 6 illustrates such an embodiment of a collapsible structure 600. The collapsible structure 600 has a top layer 602, a bottom layer 604 and cell walls 606 extending between the top layer 602 and the bottom layer 604. The cell walls 606 are adhered to the top layer 602 and the bottom layer 604 at the node 620, and cells 610 are defined by the cell walls 606, a portion of the top layer 602 and a portion of the bottom layer 604. In some embodiments, a collapsible structure may be constructed from a single layer. FIG. 7 illustrates a collapsible structure 700 constructed from a single layer 702 according to an embodiment. The single layer 702 may be folded such that it can act as both a top layer and a bottom layer. The single layer 702 may be adhered to itself at valleys and peaks 720, such that cells 710 are formed.

Any different layers of any collapsible structures described in this section or elsewhere in the specification (e.g., top layers, bottom layers, intermediate layers, etc.) may be adhered to each other by adhesive, heat welding, radio frequency welding, laser welding, or ultrasonic welding. Any layers of any collapsible structure described in this section or elsewhere in the specification may be constructed from flexible film material, for example polyurethane. Additionally, any of the collapsible structure may be constructed from a transparent material such that the user of the collapsible structure or the wound closure device can adjust the collapsible structure relative to the wound, and monitor the wound or tissue beneath the collapsible structure.

Any of the collapsible structures described herein this section or elsewhere in the specification may be constructed using any suitable methods. For example, the collapsible structures may be constructed via molding or may be printed directly using 3D printing technology. In certain embodiments, the collapsible structures of FIGS. 2A-C may be constructed from a single polymer via 3D printing. In some embodiments, the collapsible structures may be constructed from one polymer, two polymers, three polymers, or more than three polymers. The collapsible structures may be constructed from any material disclosed in this section or elsewhere in the specification.

Collapsing of Collapsible Structures

As described in elsewhere in the specification, any of collapsible structures described in this section or elsewhere in the specification may collapse by collapsing one or more cells. Each of cells is inflatable as described elsewhere in the specification, and inflated cells may collapse when they are deflated.

Figure 8A:
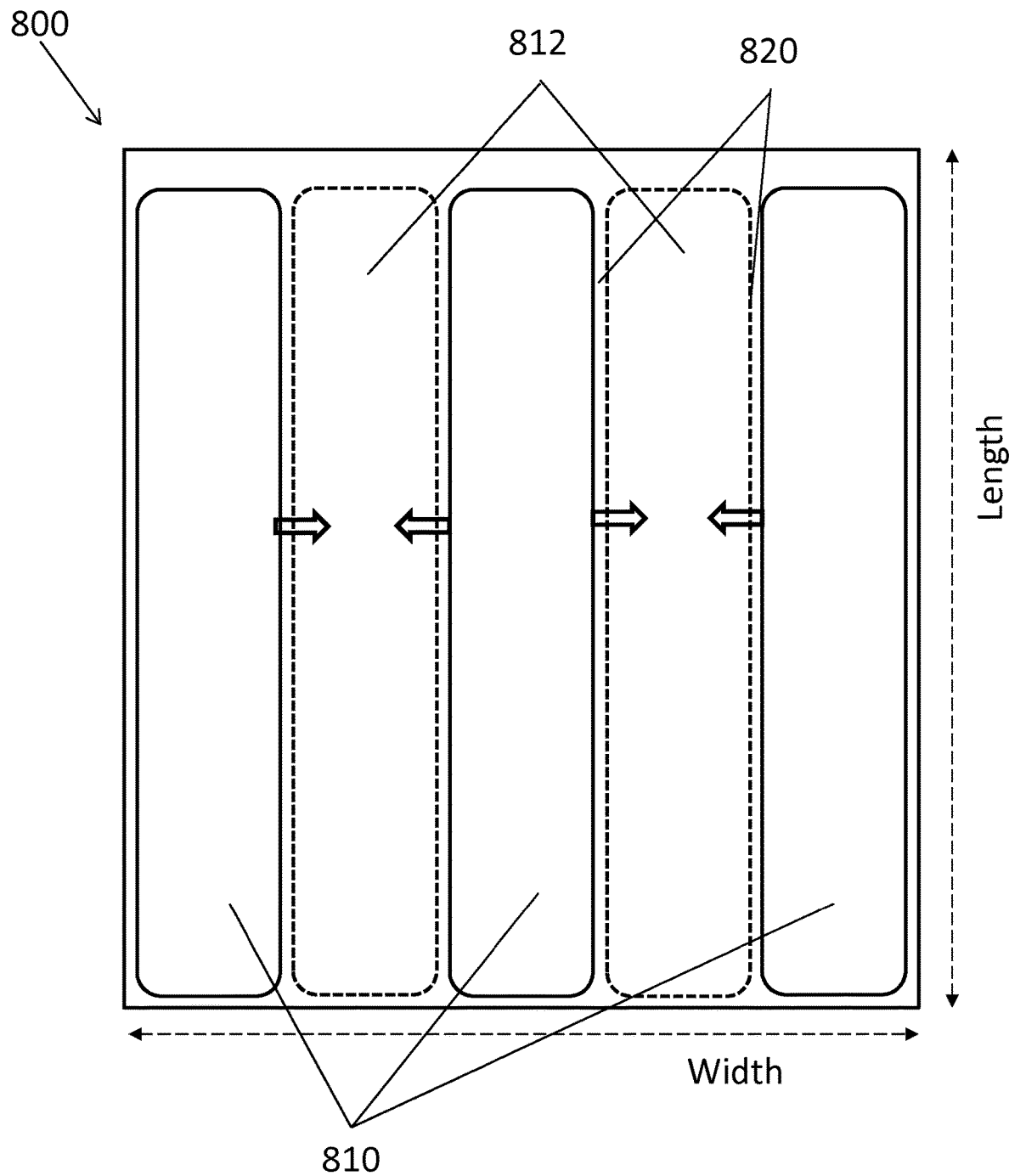
FIG. 8A illustrates collapse of a collapsible structure according to an embodiment.
Figure 8B:
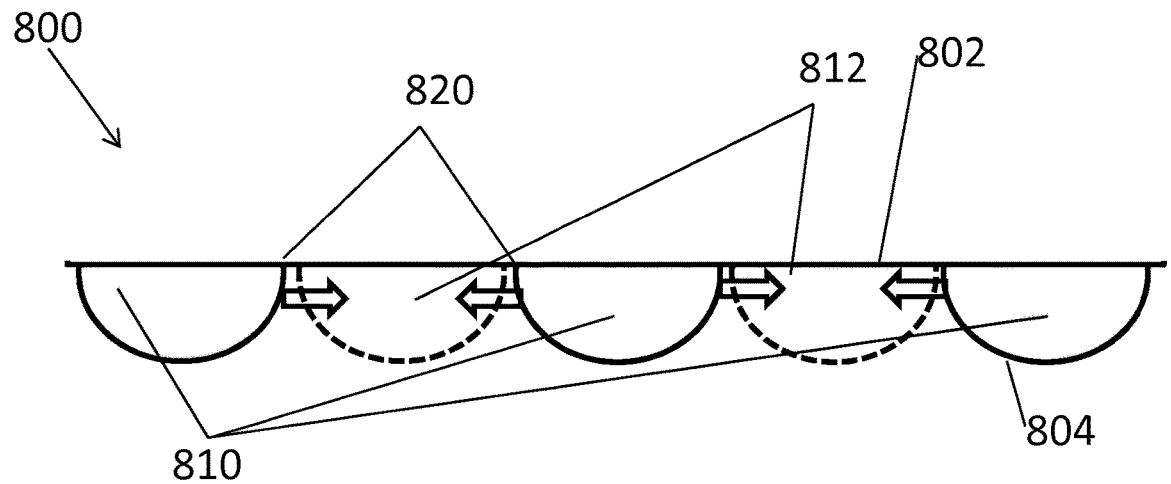
FIG. 8B illustrates a cross-sectional view of the collapsible structure of FIG. 3A.
Figure 8C:
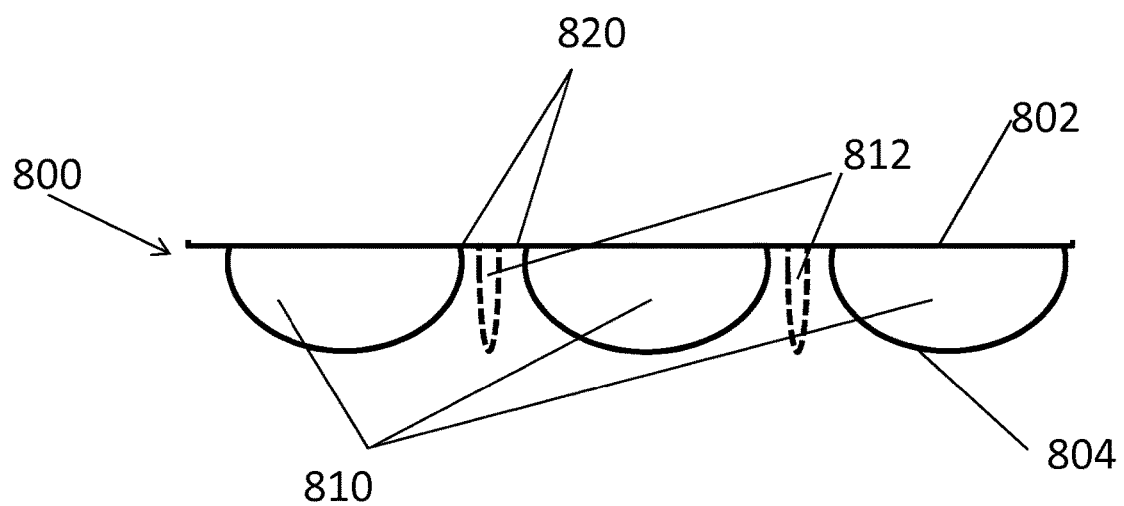
FIG. 8C illustrates a cross-sectional view of the collapsible structure of FIG. 3A in a collapsed state.

FIGS. 8A-C illustrate collapsing of an embodiment of a collapsible structure 800 similar to the collapsible structures described in relation with FIGS. 2A-C. FIGS. 8A-B are a top view of the collapsible structure 800 and a cross sectional view of the collapsible structure 800 along its width, respectively. The collapsible structure 800 includes a top layer 802, a bottom layer 804, and a plurality of elongate cells 810 arranged side-by-side along the length of the collapsible structure 800 and parallel to one another. Cells 810 are defined by valleys 820 and spaces between the top layer 802 and the bottom layer 804. As described elsewhere in the specification, cells 810 may be fluidically isolated such that each of cells 810 can be selectively deflated. In the illustrated embodiment, two cells 812 illustrated by dashed line are being deflated. In some embodiments, one, three, four or more cells can be deflated. In some embodiments, each or at least some of cells may be configured to be deflated only partially. Cells 812 may be deflated, for example, by exposing the interior volume of a cell to the exterior atmospheric environment. In some embodiment, cells 812 may be deflated by puncturing. In some embodiments, each of cells 812 may comprise retractable closure, such as a tab, covering one or more holes, such that cells can be deflated by pulling the tab and exposing the hole on the cells to the atmosphere. In some embodiments, at least some of the deflated cells 812 may be exposed to negative pressure, further deflating cells 812.

In some embodiments, when negative pressure is applied, for example, beneath the collapsible structure 800, deflated cells 812 may collapse in the direction of the arrows illustrated on FIGS. 8A-B. FIG. 8C illustrates the collapsible structure 800 in collapsed state. In collapsed state, the width of deflated cells 812 may decrease and non-deflated cells may get closer to each other as shown in FIG. 8C. As shown in FIGS. 8A-B, each of cells 812 may collapse mostly in one direction along the width of the collapsible structure 800, and thus the collapsible structure 900 may mostly collapse along its width. In some embodiments, the collapsible structure 800 may collapse more along its width rather than its length and/or height. Cells 812 may not collapse across the length and/or height because inflated elongate cells 810 will maintain their structure and the collapsible structure will substantially resist collapse along its length and/or height. In certain embodiment, direction of collapse may be changed by changing arrangement and/or the shape of cells to accommodate the type and the shape of the wound. For example, in some embodiments, the collapsible structure may collapse substantially along its width, instead of the length.

A wound closure device may include collapsible structures 800 or any other collapsible structures described in the specification. The collapsible structure may facilitate wound closure by collapsing one or more cells. For example, in certain embodiments, the collapsible structure 800 may be placed on and/or in the wound. The collapsible structure 800 may be oriented such that the lengths of the elongate cells 810 are aligned with the length of the wound. In some embodiments, a tissue protection layer can be placed in the wound and then the collapsible structure can be placed above the tissue protection layer. The collapsible structure 800 may be fixed on and/or in the wound by attaching the collapsible structure to the tissue surrounding the wound for example with adhesives. Deflating one or more cells, such as one or more cells 812, can result in the collapsible structure 800 collapsing along the width of the collapsible structure, facilitating the closure of the wound across its width by drawing the edges of the wound closer. Additional cells can be deflated and/or one or more collapsed cells can be deflated further during the course of treatment of the wound as the wound is closing and additional collapse is required.

Any of collapsible structures and wound closure devices described in this section or elsewhere in this specification may collapse on a variety of timescales in a dynamic fashion. In certain embodiments, the majority of the collapse may occur within the first few minutes upon application of negative pressure. However, after the initial collapse, the collapsible structure or wound closure device may continue to collapse at a much slower rate, thereby applying increasing tension over a long period of time and drawing the edges of the wound closer together. By slowly drawing the wound edges closer together over time, the collapsible structure or wound closure device allows the surrounding healing tissue to remodel synergistically with the closure of the device or collapsible structure. Slow, dynamic wound closure may allow the surrounding tissue to heal at an accelerated rate, because the collapsing sheet or device slowly brings the edges of the wound closer together without stressing the newly formed or weakened tissue too quickly.

In certain embodiments, up to 90% of the collapse of the collapsible structure or wound closure device may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the collapsible structure can collapse at a variable rate. In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

Figure 9:
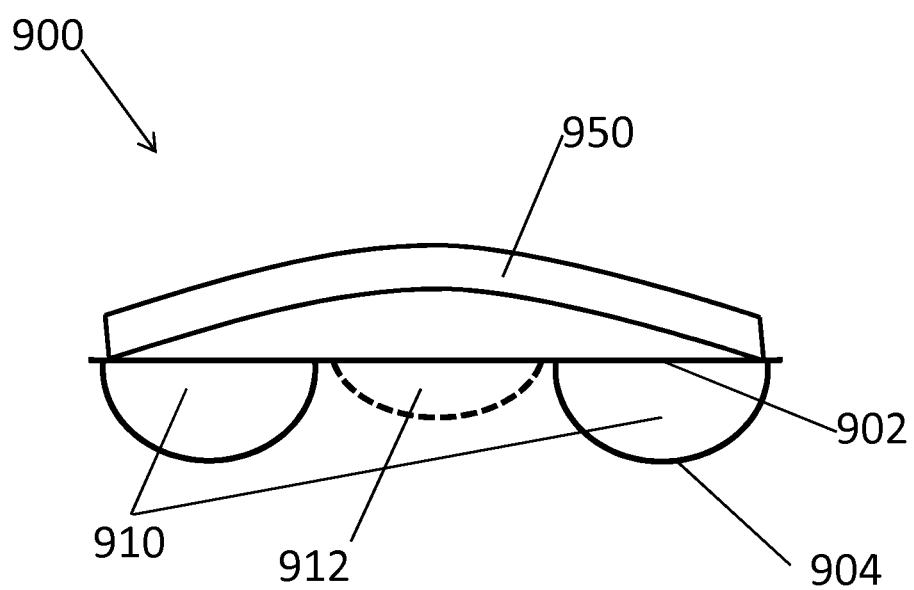
FIG. 9 illustrates an embodiment of a collapsible structure with an attachment.

FIG. 9 illustrates a cross-sectional view of an embodiment of a collapsible structure 900 similar to the collapsible structures described in relation with FIGS. 2A-C and 8A-C. The collapsible structure 900 has a top layer 902, a bottom layer 904, cells 910 as collapsible structures of FIGS. 2A-C and 8A-C, and a cell 912 is being deflated. Here, the collapsible structure 900 additionally contains a support or suspender 950 which keeps the cells 910 apart, such that the collapsible structure 900 does not substantially collapse or undergoes a limited collapse upon deflation of the cell 912. In some embodiments, the suspender 950 may be reversibly attached to the top layer 902 of the collapsible structure. In some embodiments, the suspender 950 may be a "stick-on" patch.

Inflating/Deflating Collapsible Structures

Figure 10:
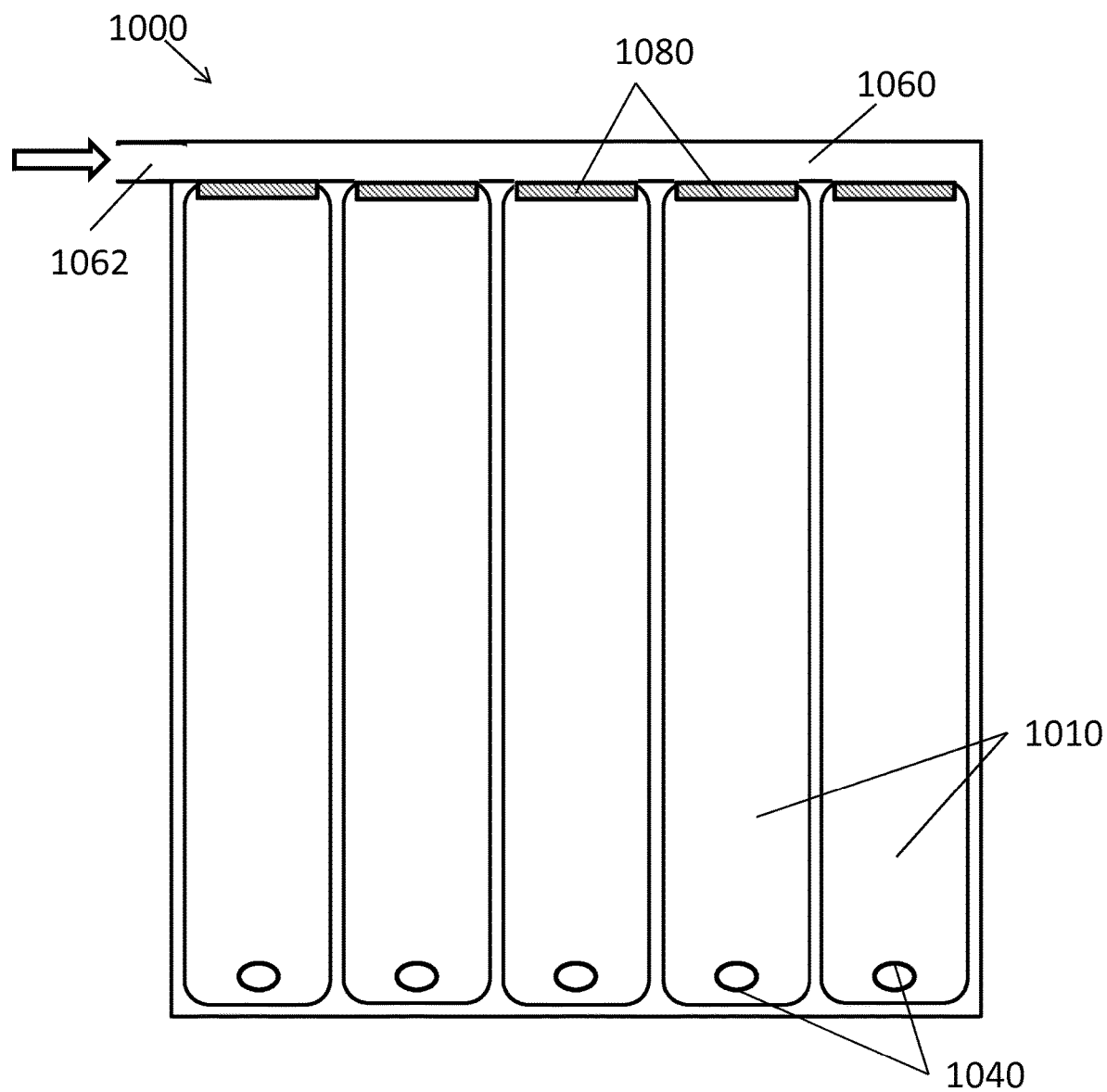
FIG. 10 illustrates an embodiment of a collapsible structure.

As described in this section or elsewhere in the specification, a plurality of cells of a collapsible structure may be individually/selectively inflated and/or deflated. FIG. 10 illustrates a schematic view of such an embodiment of a collapsible structure 1000 similar to the collapsible structures described in relation with FIGS. 2A-C and 8A-C. The collapsible structure 1000 includes a plurality of elongate cells 1010 as described herein. The collapsible structure 1000 also includes a fluid channel 1060, such as an air channel. In some embodiments, the air channel 1060 may be opened to the source of the air and be fluidically connected to each (or some) of the cells 1010, such that each (or some of the) cell 1010 may be inflated by air coming through the air channel 1060. In some embodiments, an opening 1062 of the air channel may be reversibly sealed, such that cells 1010 are not unintentionally deflated.

In some embodiments, the collapsible structure 1000 may have one or more seal section 1080 at the junction between each or some of the cells 1010 and the air channel 1060. In some embodiments, the seal sections 1080 are configured to be sealed by pressing, such that at least one of the cells 1010 may not be inflated even when air comes through the air channel 1060. Seal sections 1080 may be sealed for example by adhesives, Velcro®, plastic zippers or any other suitable mechanisms. In some embodiments, seal sections 1080 may be reversibly sealed, such that they can be re-opened to make cells inflatable. In some embodiments, seal sections 1080 may be sealed after the cells 1010 have been inflated, such that cells do not deflate. Seal sections 1080 may be configured to withstand the air pressure within inflated cell 1010, such that it does not get opened unintentionally after it is sealed.

The collapsible structure 1000 may include mechanisms to selectively deflate cells 1010. In some embodiments, inflated cells 1010 may be punctured to selectively deflate cells. Inflated cells 1010 may also be deflated without puncturing cells. For example, each (or some) of the cells 1010 may have a closure (which may be reversible), such as pull-off tabs 1040 on the top layer and/or the bottom layer. In some embodiments, pull-off tabs 1040 include a pre-cut on the top layer and/or the bottom layer of the cell. When any of pull-off tabs 1040 are pulled off, the cell where the tab 1040 is located will be deflated. With the pull-off tabs 1040, one may deflate the accidentally inflated cells, or deflate cells to collapse the collapsible structure. In some embodiments, pull-off tabs 1040 may be pulled off reversibly, such that cells can be deflated and inflated multiple times. For example, pull-off tabs 1040 may include a pre-made hole on the top layer or the bottom layer, and a detachable tab covering the hole.

Figure 11A:
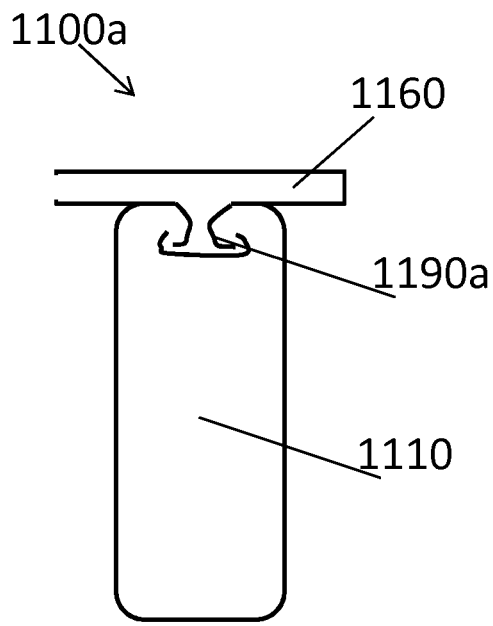
FIGS. 11A-C illustrate embodiments of a collapsible structure.
Figure 11B:
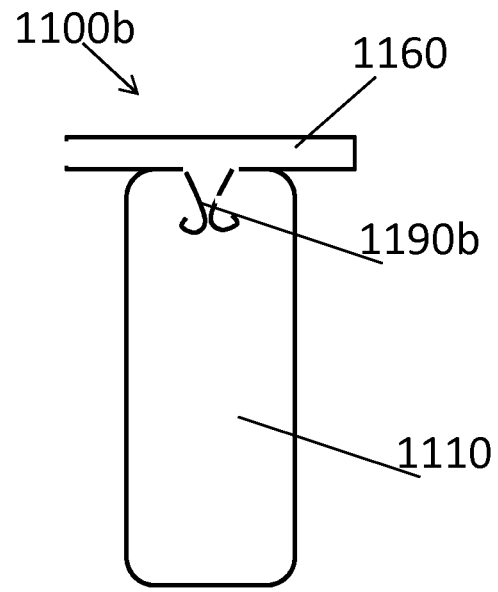
Figure 11C:
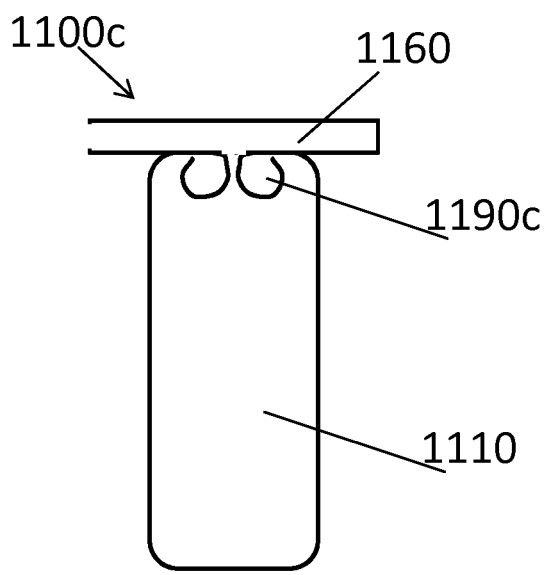

In addition to, or alternatively to the foregoing, collapsible structures may have a mechanism that permits inflated cells to be sealed without manually sealing junctions between the air channel and the cell. For example, in some embodiments, a collapsible structure includes one or more one-way or non-return valves at one or more junctions between an fluid channel (which can be an air channel) and a cell. FIG. 11A-C illustrate partial schematic views of various examples of such embodiments, where collapsible structures 1100a, 1100b, and 1100c have different types of non-return valves 1190a, 1190b, and 1190c, respectively, at the junction of an air channel 1160 and a cell 1110. Air may flow from the air channel 1160 to the cell 1110 through no-return valves, but air may not flow the other way. Therefore, cells may not be deflated through the air channel 1160.

Non-Planar Collapsible Structures

Figure 12:
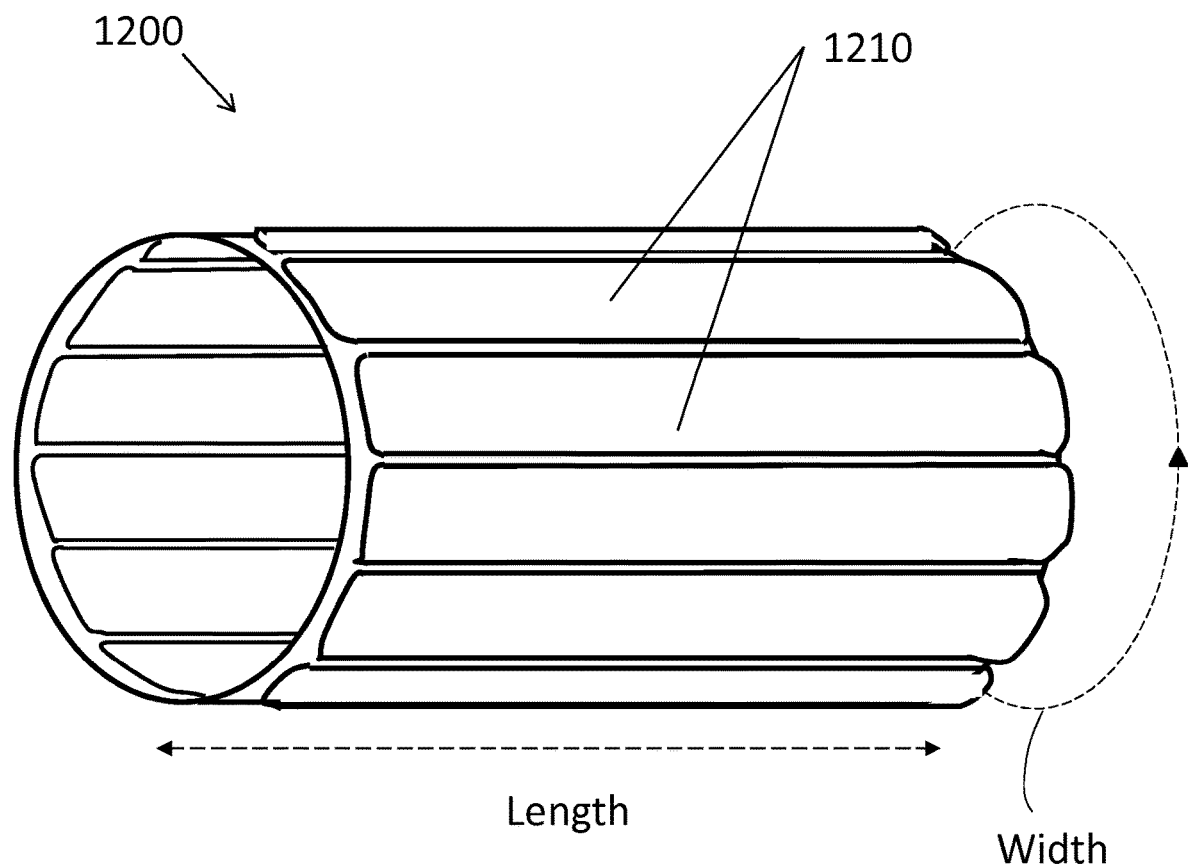
FIG. 12 illustrates an embodiment of a collapsible structure.

While the collapsible structures illustrated in FIGS. 2-10 are planar or have approximately rectangular shape, collapsible structures may have any shape while having any features of collapsible structures described in this section or elsewhere in the specification. For example, a collapsible structure may have cylindrical or domed shape to better accommodate the wound. FIG. 12 illustrates a cylindrical collapsible structure 1200 containing the plurality of elongate cells 1210 that are annularly arranged side-by-side. The cylindrical collapsible structure 1200 may be useful in closing the wound on limbs, such as an amputation limb.

Figure 13:
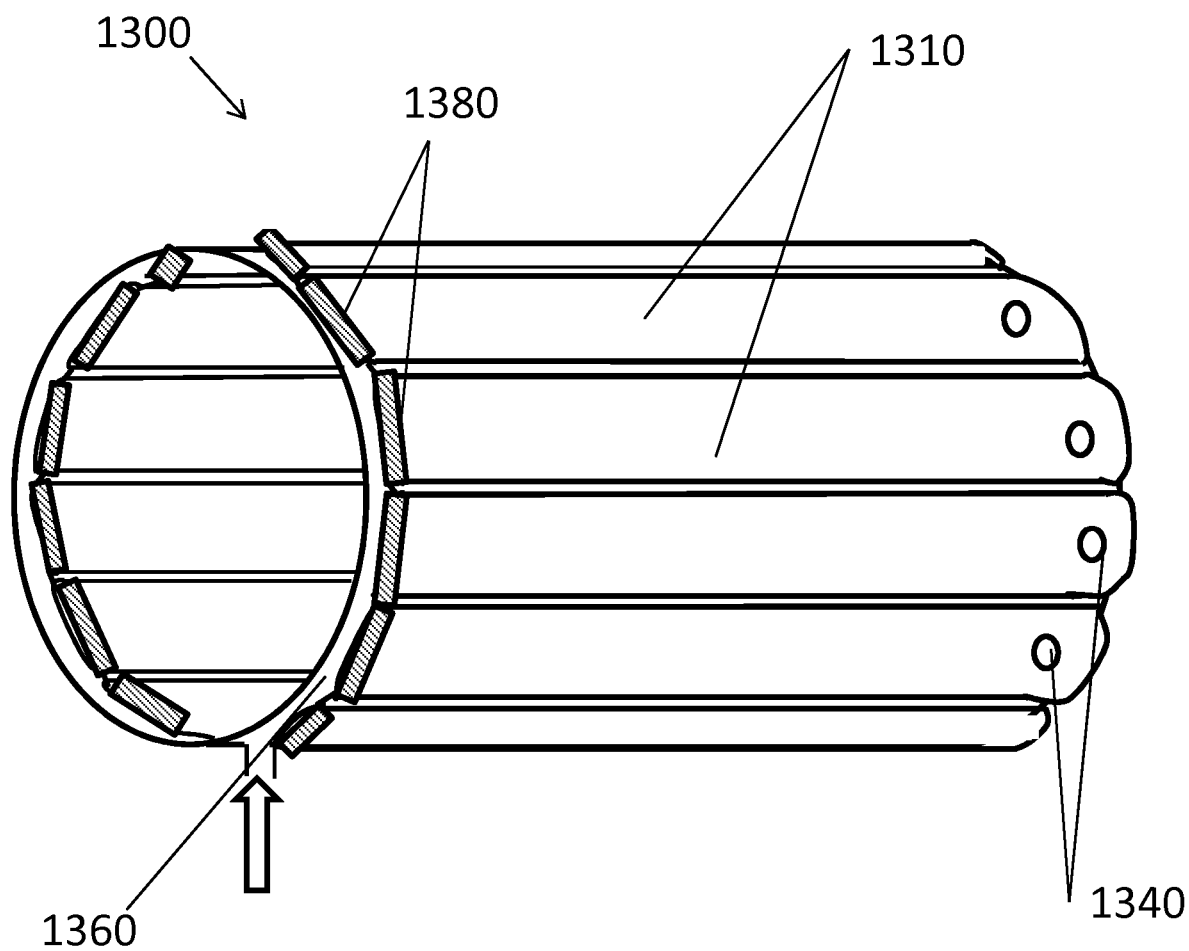
FIG. 13 illustrates an embodiment of a collapsible structure.

The collapsible structure 1200 may have any features or configurations described in this section or elsewhere in the specification. For example, cells of the cylindrical collapsible structure may be individually/selectively inflated and/or deflated. FIG. 13 illustrates such an embodiment of a collapsible structure 1300 having a plurality of elongate cells 1310, a fluid channel 1360, which can be similar to the fluid channel 1060 of FIG. 10, a plurality of seal sections 1380 similar to the plurality of seal sections 1080 of FIG. 10, and a plurality of pull-off tabs 1340 similar to the plurality of pull-off tabs 1040 of FIG. 10. The fluid channel 1360 can be an air channel.

Figure 14A:
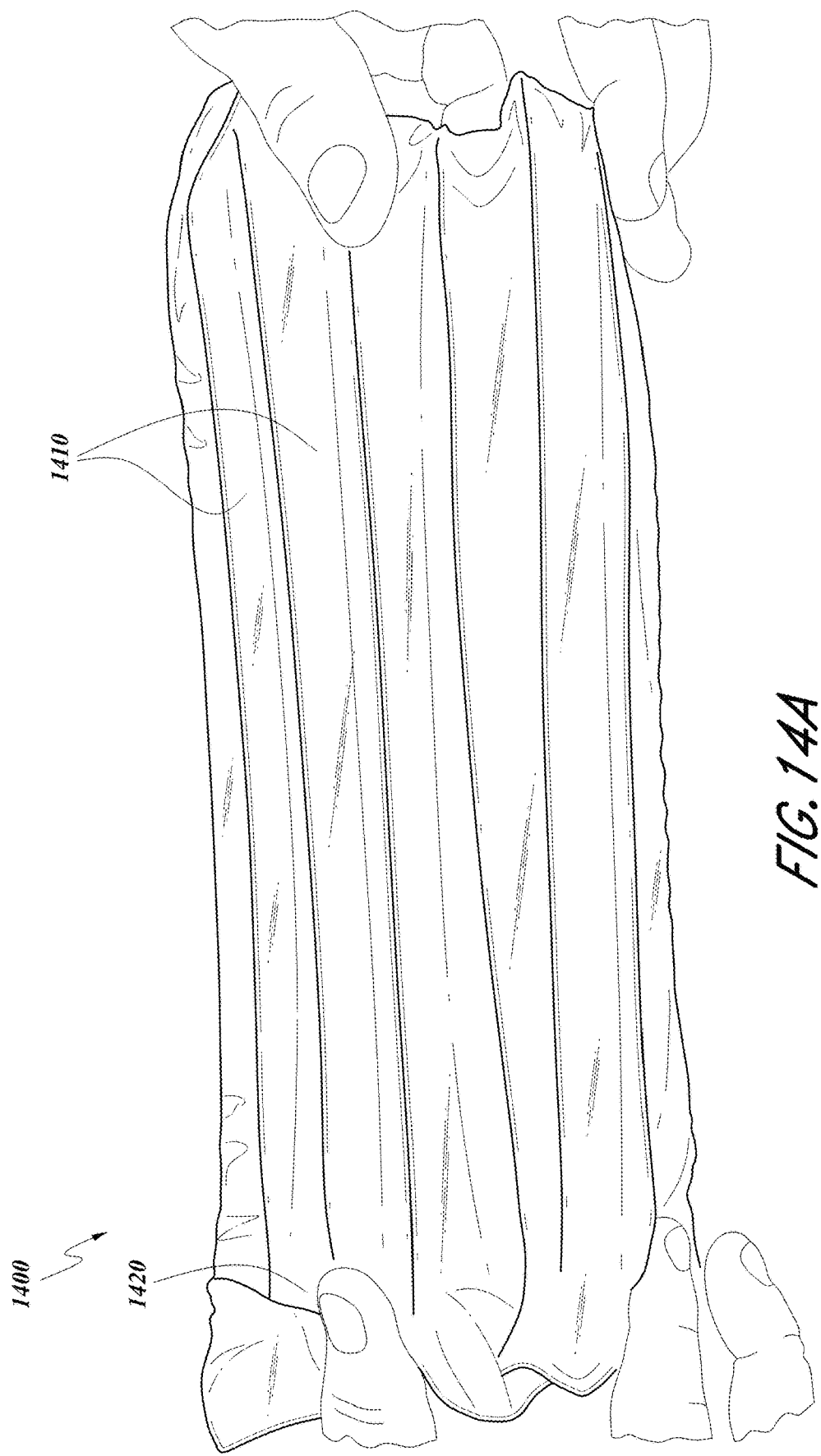
FIGS. 14A-E are photographs of an embodiment of a collapsible structure.
Figure 14B:
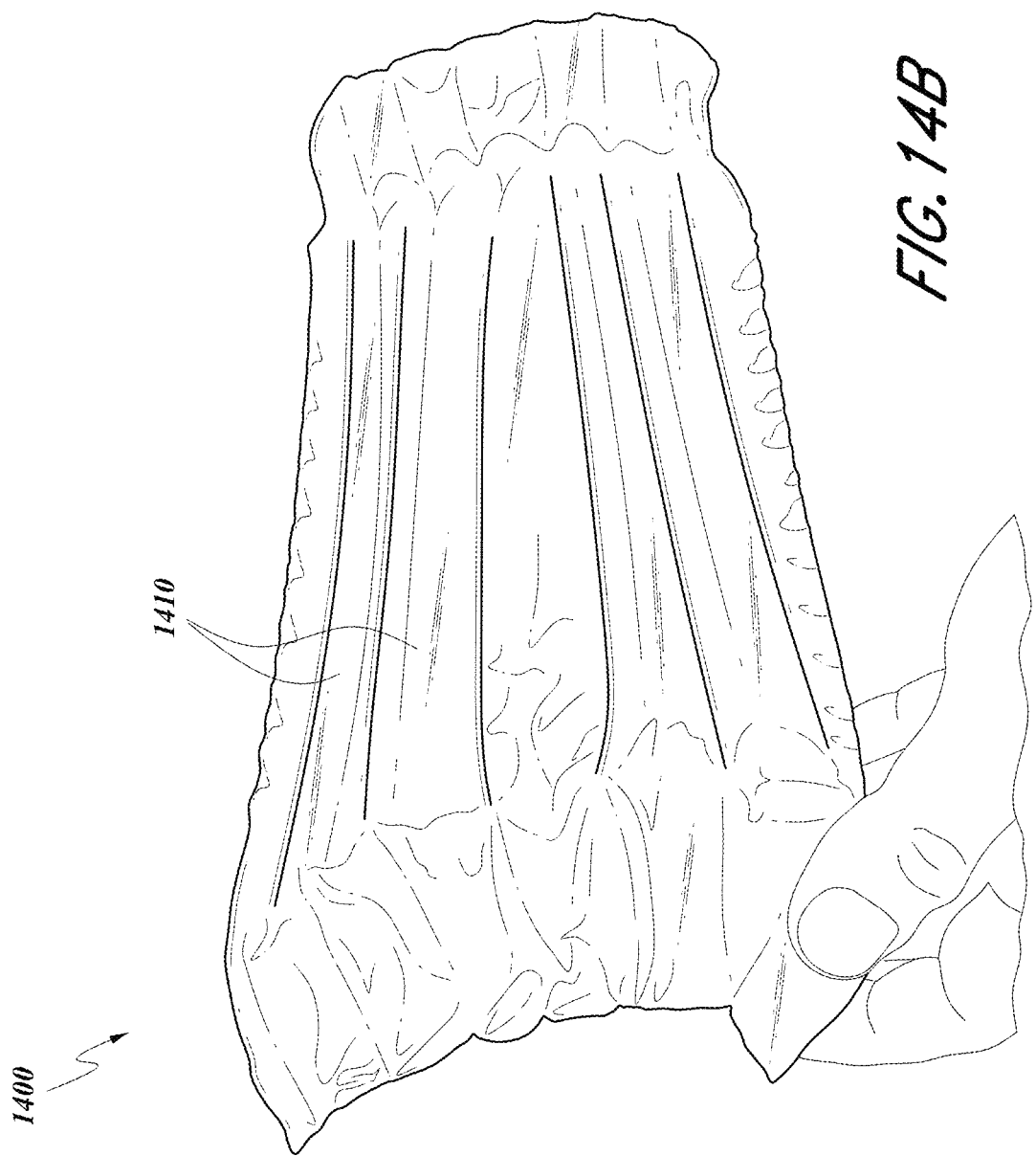
Figure 14C:
Figure 14D:
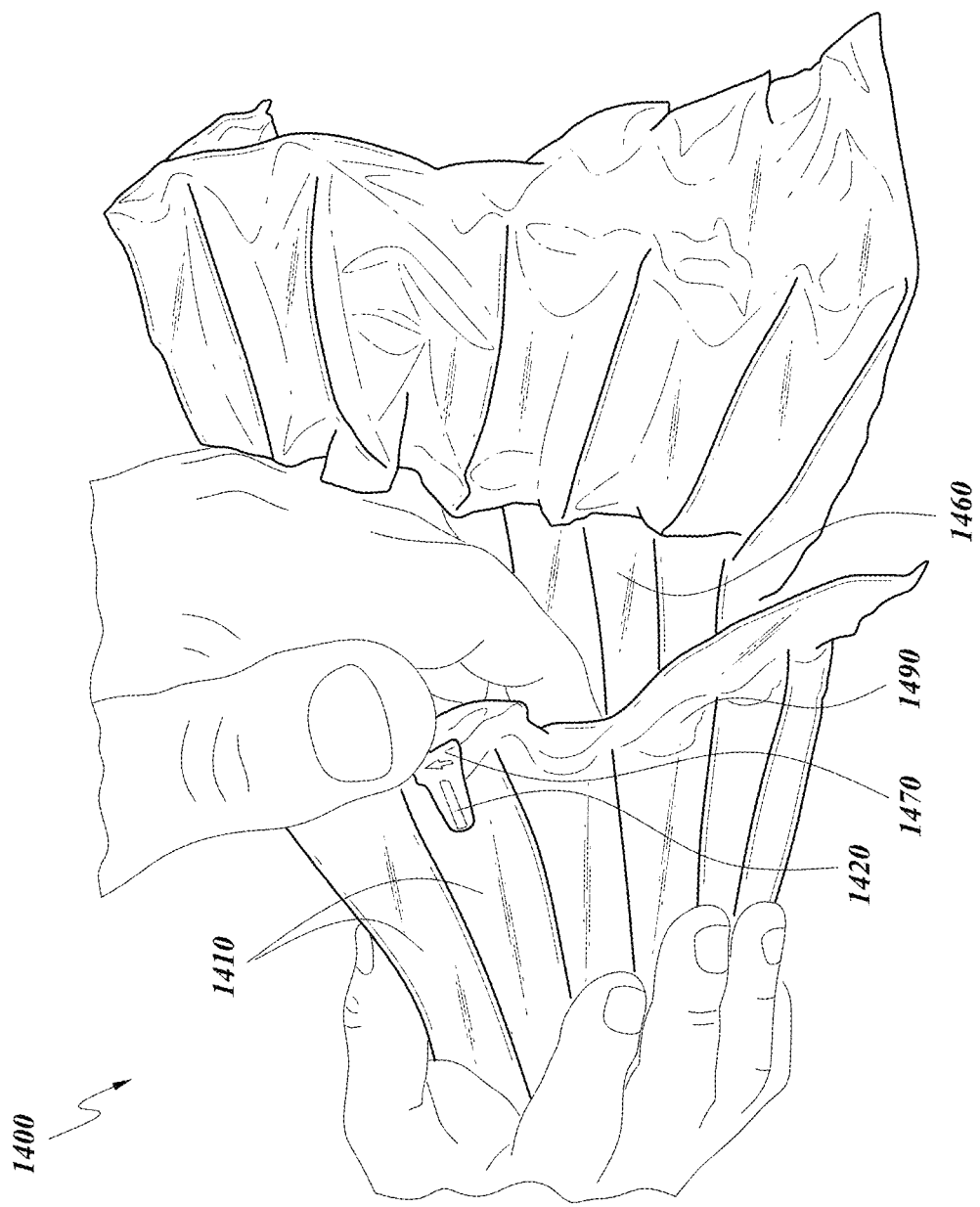
Figure 14E:
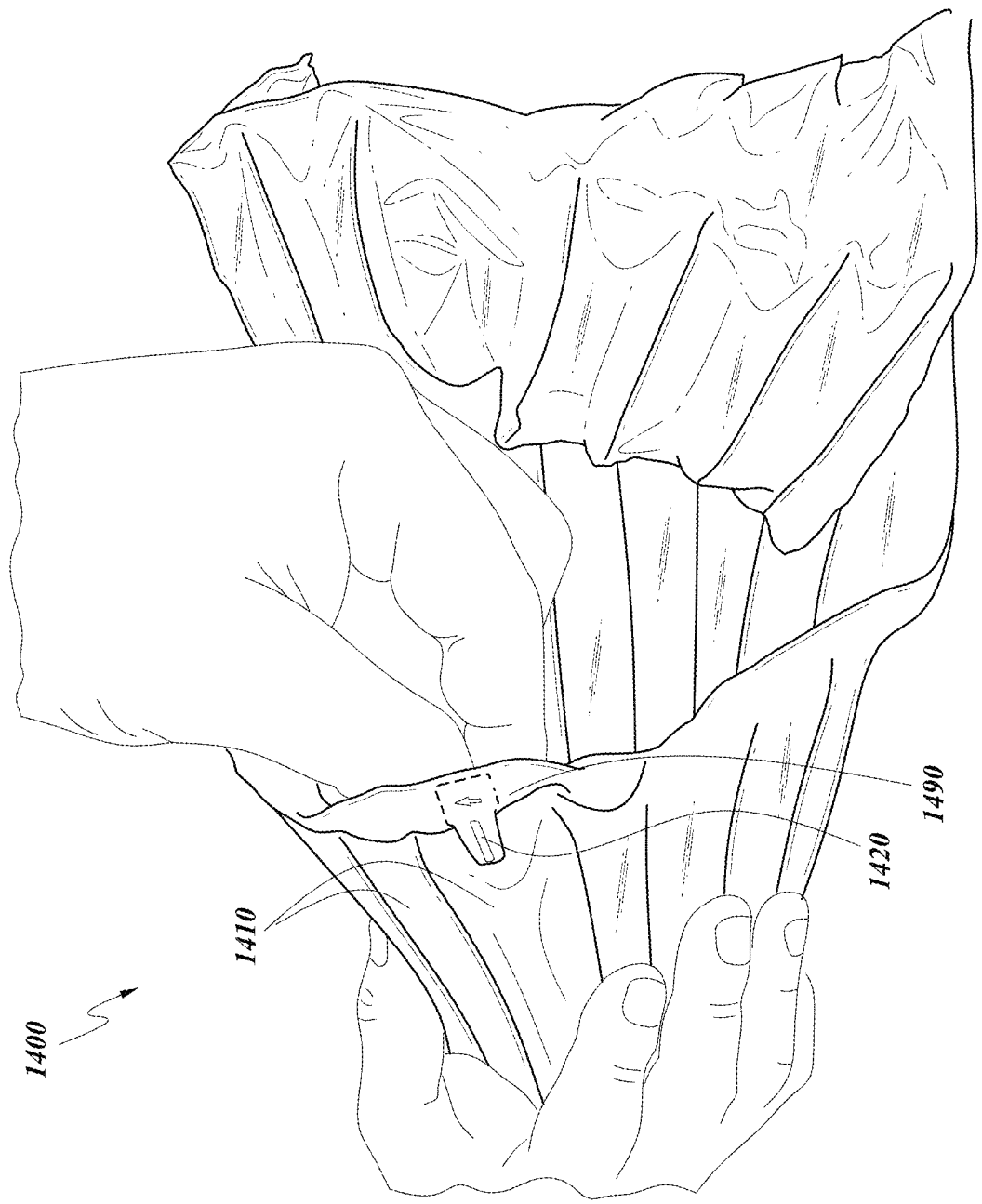

FIGS. 14A-14E are photographs of an embodiment of a collapsible structure 1400 having a plurality of elongate cells 1410. The collapsible structure 1400 has substantially cylindrical shape and is similar with the cylindrical collapsible structures described in relation with FIGS. 12 and 13. Here, the collapsible structure is closed at one end as shown in FIG. 14C. A closed-ended collapsible structure may better accommodate wounds at the extremities, while open-ended collapsible structure may better accommodate wounds at upper limbs. The collapsible structure 1400 may have a cavity 1460 enclosed by the collapsible structure and its closed-end, and the body part containing a wound, for example the extremities, may go into the cavity 1460. In some embodiments, as shown in FIGS. 14B-D, elongate cells 1410 extend through the closed end to reach the other side of the collapsible structure across the cavity 1460 (for example, wrap around the collapsible structure) while an fluid channel 1490 only extends through a portion of the cylindrical collapsible structure 1400 (such as, the front side of the structure as illustrated in FIG. 14D). The fluid channel 1490, which can be an air channel, may inflate the channels along their entire length even through the air channel only covers about half of the structure. The collapsible structure 1400 also includes seal sections 1420, such that cells 1410 can be sealed and prevented from inflating. In some embodiments, the seal sections 1420 may include a self-valving element, and would not need to have another component to act as a valve. The self-valving element may include a closure, such as a tab 1470 shown in FIG. 14D. The tab may be pulled in a particular direction, and may have indications, such as a printed sign to let the use know where the force should be applied. The printed sign may be arrows, numbers, color code, or in any other suitable form which can inform the user about the direction of applying the force.

Figure 15:
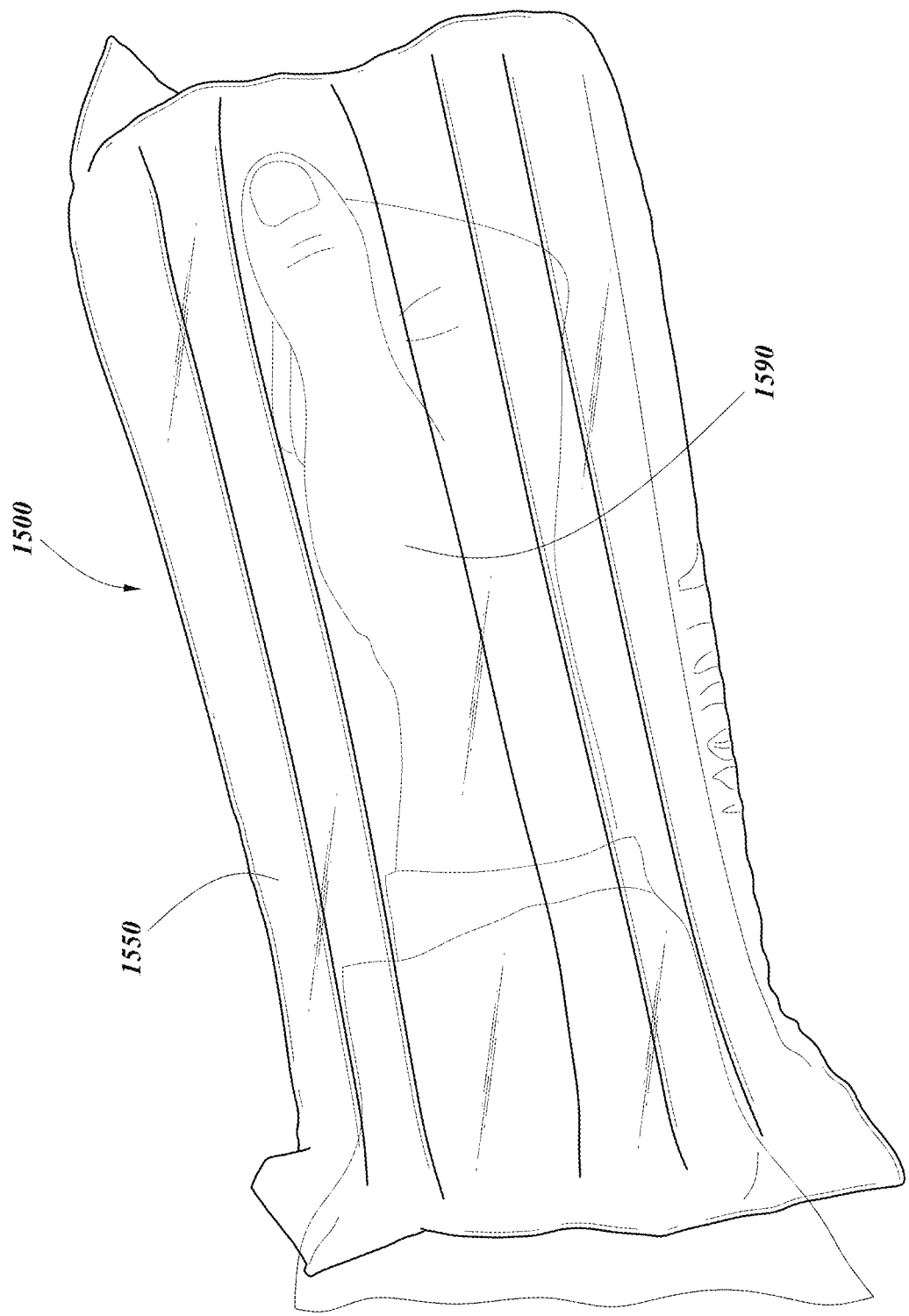
FIG. 15 is a photograph of an embodiment of a collapsible structure applied to an arm.

As described elsewhere in the specification, a collapsible structure may be applied on wounds at extremities. FIG. 15 is a photograph of an embodiment of a wound closure device 1500 including collapsible structure 1550 similar to the collapsible structure 1400 of FIGS. 14A-E, applied on a human arm 1590. In some embodiments, a tissue protection layer (not shown) may be first applied on the wound, and then the collapsible structure 1550 may be applied over the tissue protection layer. In some embodiments, negative pressure may be provided between the arm 1590 (that is, the wound) and the collapsible structure 1550. The collapsible structure 1550 may be adhered to the arm, for example, at the perimeter of the opening for the insertion of the arm into the structure 1550, and form a fluid-tight seal around the wound, such that negative pressure is maintained. A conduit (not shown) or a port (not shown) may be further included (for example, on the collapsible structure) to supply negative pressure to and/or under the collapsible structure 1550. In some embodiments, a drape (not shown) may be applied over the collapsible structure 1550.

Figure 16A:
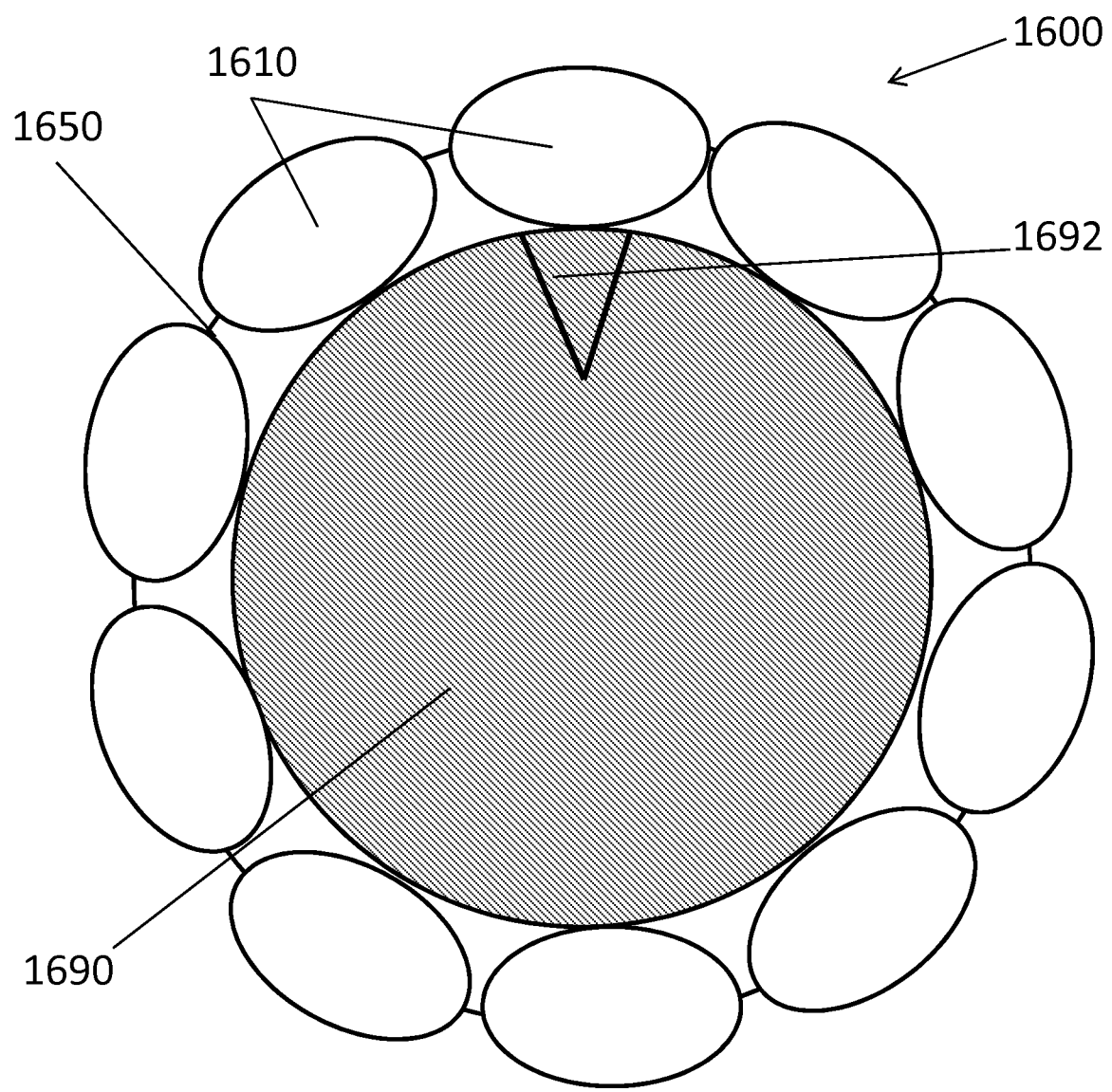
FIG. 16A illustrates an embodiment of a collapsible structure applied to an amputation wound.

FIG. 16A illustrates a cross sectional view of an embodiment of a wound closure device 1600 similar to the wound closure device 1500 of FIG. 15. The device 1600 includes a collapsible structure 1650 similar to the collapsible structures described in relation with FIGS. 12-15, with the collapsible structure applied around a limb 1690 having a wound 1692. The collapsible structure 1650 includes cells 1610.

Figure 16B:
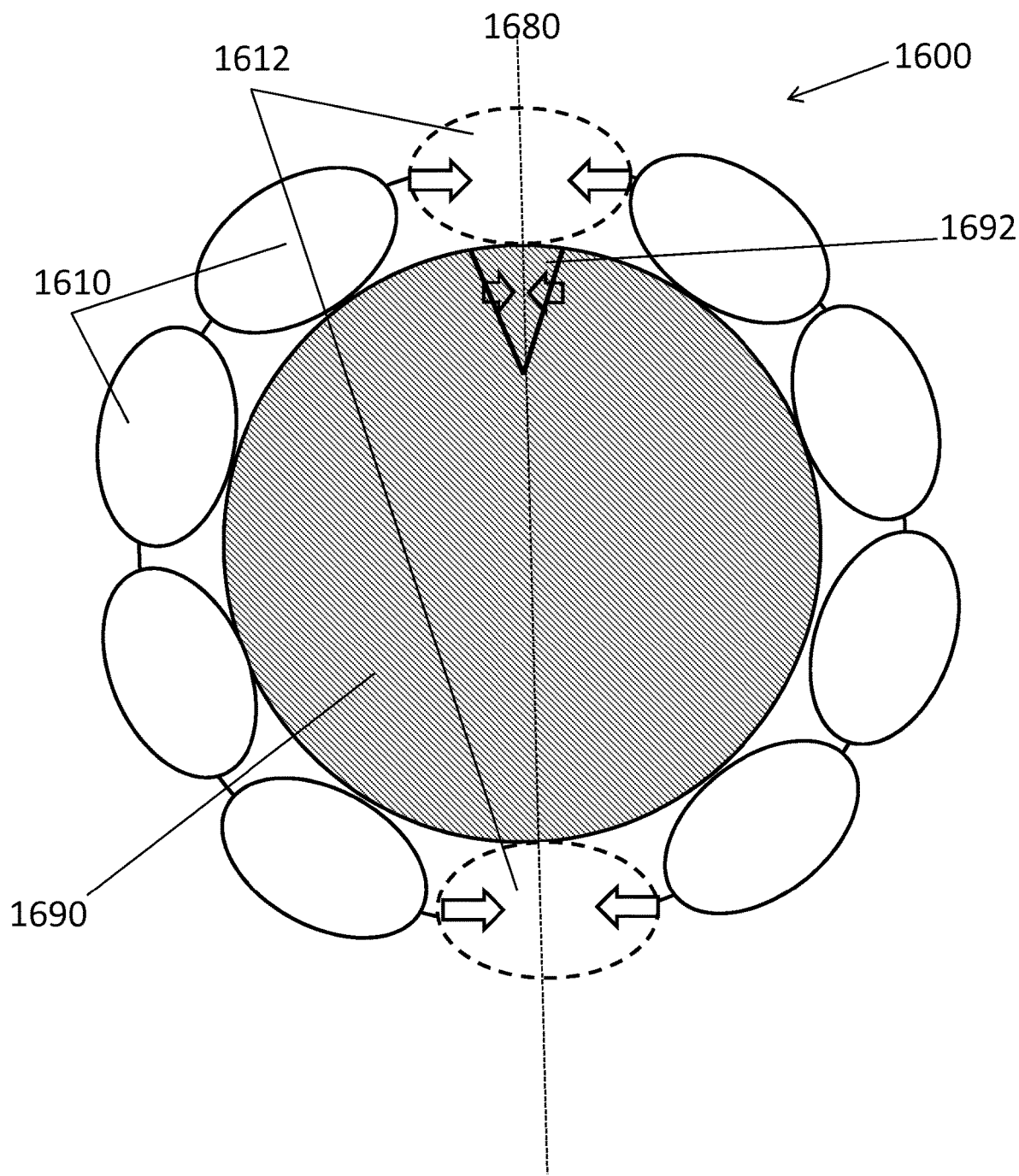
FIG. 16B illustrates collapse of the collapsible structure of FIG. 16A.

FIG. 16B illustrates collapse of the wound closure device 1600 of FIG. 16A and closure of the wound 1692. When cells 1612 are deflated by any suitable methods described in this section or elsewhere in the specification, the cells 1612 may collapse in the direction of the arrows. Overall, the collapsible structure 1650 may collapse in the direction of the arrow, toward an imaginary plane 1680 along the length of the cells 1610. As the collapsible structure 1650 collapses, it may apply a force in the direction of arrows to the wound 1692, facilitating the closure of the wound 1692.

Other Variations

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (e.g., of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A wound closure device comprising a collapsible structure, the collapsible structure comprising:
   a top layer and a bottom layer, wherein the top layer and the bottom layer are partially adhered to each other;
   a volume between the top layer and the bottom layer; and
   a plurality of elongate cells each having a length and a width, the plurality of elongate cells arranged side-by-side in at least a portion of the volume, the cells in the plurality of elongate cells arranged parallel to one another,
   wherein:
      said plurality of elongate cells are defined by at least one of the top layer and the bottom layer,
      the wound closure device is configured to create a sealed space over a wound and configured to receive negative pressure in the sealed space,
      each of said plurality of elongate cells is configured to be fluidically isolated such that a deflation of one of the plurality of elongate cells does not cause a deflation of any other elongate cells of the plurality of elongate cells,
      at least one of the cells is inflatable and deflatable; and
      the wound closure device is configured such that deflating one or more of the plurality of elongate cells results in the wound closure device collapsing along a width of the collapsible structure, thereby facilitating a closure of the wound across a width of the wound by drawing edges of the wound closer together.

2. The device of claim 1, wherein the collapsible structure is configured to collapse under negative pressure when at least one of the cells is deflated.

3. The device of claim 2, wherein the collapsible structure is configured to collapse along a length of the collapsible structure.

4. The device of claim 1, wherein the top layer and the bottom layer comprise a flexible film material.

5. The device of claim 1, wherein a length of each cell is greater than the width of each cell.

6. The device of claim 1, wherein the collapsible structure has at least partially a cylindrical shape, and wherein the cells are arranged such that the widths of the cells are positioned substantially annularly around a circular side of the cylindrical shape.

7. The device of claim 6, wherein the collapsible structure is closed at one end of the cylindrical shape.

8. The device of claim 1, wherein the collapsible structure further comprises an intermediate layer, wherein each cell is defined by the intermediate layer and either one of the top layer or the bottom layer, and wherein the intermediate layer is at least partially adhered to each of the top layer and the bottom layer.

9. The device of claim 1, wherein the top layer, the bottom layer and an intermediate layer are at least partially adhered to each other by welding.

10. The device of claim 9, wherein welding is selected from the group consisting of heat welding, radio frequency welding, laser welding, and ultrasonic welding.

11. The device of claim 1, wherein the collapsible structure further comprises a fluid channel configured to fluidically connect said plurality of cells with an environment exterior to the collapsible structure.

12. The device of claim 11, wherein at least one of the cells comprises a seal between the fluid channel and the cell.

13. The device of claim 11, wherein at least one of the cells comprises a valve between the fluid channel and the cell, and wherein the valve is configured to permit fluid flow only from the fluid channel to the cell but not in the other direction.

14. The device of claim 1, wherein at least one of the cells comprises a pull-off tab configured to provide a fluidic connection between the cell and environment exterior to the collapsible structure.

15. The device of claim 14, wherein the pull-off tab is configured to be reversible.

16. The device of claim 1, further comprising a tissue protection layer.

17. The device of claim 1, further comprising one or more drapes configured to cover the collapsible structure and form a seal around a wound.

18. The device of claim 1, further comprising a suction port configured to supply negative pressure to the wound.

19. The device of claim 1, further comprising a negative pressure source configured to supply negative pressure to the collapsible structure to cause collapse of the collapsible structure and cause the collapsible structure to apply a force to the wound.

20. A method of treating a wound, comprising:
placing a collapsible structure in or over the wound so that a length of the collapsible structure is aligned along the length of the collapsible structure with a length of the wound, wherein the collapsible structure comprises:
a top layer and a bottom layer, wherein the top layer and the bottom layer are partially adhered to each other;
a volume between the top layer and the bottom layer; and
a plurality of elongate cells each having a length and a width, the plurality of elongate cells arranged side-by-side in at least a portion of the volume, the cells in the plurality of elongate cells arranged parallel to one another,
wherein:
said plurality of elongate cells are defined by at least one of the top layer and the bottom layer,
the wound closure device is configured to create a sealed space over a wound and configured to receive negative pressure in the sealed space,
each of said plurality of elongate cells is configured to be fluidically isolated such that a deflation of one of the plurality of elongate cells does not cause a deflation of any other elongate cells of the plurality of elongate cells, and
at least one of the cells is inflatable and deflatable;
creating a sealed space over the wound;
providing a negative pressure to the sealed space; and
drawing edges of the wound closer together along a width of the collapsible structure by deflating at least one of the plurality of elongate cells.

21. The method of claim 20, further comprising applying negative pressure through the collapsible structure to the wound via a source of negative pressure, wherein the application of negative pressure causes the collapsible structure to collapse.

22. The method of claim 20, further comprising inserting a tissue protection layer over the wound before placing the collapsible structure.

23. The device of claim 1, wherein the collapsible structure has a non-planar shape in a direction that is orthogonal to the length of each of the plurality of elongate cells.

24. The device of claim 1, wherein the wound closure device is configured for use without any conduits in communication with the plurality of elongate cells.

25. A method of treating a wound, comprising:
inflating a plurality of elongate cells of a collapsible structure;
wherein:
each of the plurality of elongate cells has a length and a width;
the plurality of elongate cells are arranged side-by-side in at least a portion of the collapsible structure; and
each of said plurality of elongate cells is configured to be fluidically isolated such that an inflation of one of the plurality of elongate cells does not cause an inflation of any other elongate cells of the plurality of elongate cells and such that a deflation of one of the plurality of elongate cells does not cause a deflation of any other elongate cells of the plurality of elongate cells;
positioning the collapsible structure over the wound;
creating a sealed space over the wound;
providing a negative pressure to the sealed space; and
drawing edges of the wound closer together along a width of the collapsible structure by deflating a first one of the plurality of elongate cells, thereby facilitating a closure of the wound across a width of the wound.

26. The method of claim 20, wherein the collapsible structure is configured for use without any conduits in communication with the plurality of elongate cells.

27. The method of claim 20, wherein the collapsible structure further comprises a fluid channel configured to fluidically connect said plurality of cells with an environment exterior to the collapsible structure and wherein at least one of the cells comprises a seal between the fluid channel and the cell or a valve between the fluid channel and the cell.

28. The method of claim 20, comprising removing a pull-off tab from one or more of the plurality of elongate cells to reduce a pressure within the one or more of the plurality of cells.

29. The method of claim 20, wherein the collapsible structure has at least partially a cylindrical shape, wherein the cells are arranged such that the widths of the cells are positioned substantially annularly around a circular side of the cylindrical shape.

30. The method of claim 29, wherein the collapsible structure is closed at one end of the cylindrical shape.

31. The method of claim 20, further comprising applying the collapsible structure around a limb, wherein the collapsible structure is at least partially annularly shaped.

32. The method of claim 25, wherein at least one of the plurality of elongate cells comprises a valve.

33. The method of claim 25, wherein the collapsible structure is configured for use without any conduits in communication with the plurality of elongate cells.

34. The method of claim 25, comprising removing a pull-off tab from one or more of the plurality of elongate cells to reduce a pressure within the one or more of the plurality of cells.

35. The method of claim 25, wherein the collapsible structure has at least partially a cylindrical shape, wherein the cells are arranged such that the widths of the cells are positioned substantially annularly around a circular side of the cylindrical shape.

36. The method of claim 35, wherein the collapsible structure is closed at one end of the cylindrical shape.

37. The method of claim 25, further comprising applying the collapsible structure around a limb, wherein the collapsible structure is at least partially annularly shaped.

* * * * *